United States Patent [19]

Haber et al.

[11] Patent Number: 5,199,949
[45] Date of Patent: Apr. 6, 1993

[54] MULTIPLE PHARMACEUTICAL SYRINGE

[75] Inventors: Terry M. Haber, Lake Forest; William H. Smedley, Lake Elsinore; Clark B. Foster, Laguna Niguel, all of Calif.

[73] Assignee: Habley Medical Technology Corp., Laguna Hills, Calif.

[21] Appl. No.: 718,398

[22] Filed: Jun. 21, 1991

Related U.S. Application Data

[63] Continuation-in-part of Ser. No. 667,319, Mar. 8, 1991, and a continuation-in-part of Ser. No. 668,278, Mar. 8, 1991.

[51] Int. Cl.$^5$ ............... A61M 37/00; A61M 5/24
[52] U.S. Cl. ............................. 604/88; 604/191; 604/205; 604/237
[58] Field of Search ............... 604/82, 83, 85-90, 604/191, 192, 207, 213, 220, 232, 234, 236-238, 239, 240, 201, 205

[56] References Cited

U.S. PATENT DOCUMENTS

| | | | |
|---|---|---|---|
| 1,557,836 | 10/1925 | Hein | 604/237 |
| 3,659,587 | 5/1972 | Baldwin | 604/237 X |
| 3,696,806 | 10/1972 | Sausse | 604/191 X |
| 4,109,653 | 8/1978 | Kozam et al. | 604/191 |
| 4,738,660 | 4/1988 | Lucas | 604/139 |
| 4,755,169 | 7/1988 | Sarnoff et al. | 604/51 |
| 4,795,441 | 1/1989 | Bhatt | 604/124 |
| 4,902,281 | 2/1990 | Avoy | 604/191 |
| 5,067,948 | 11/1991 | Haber et al. | 604/213 |

Primary Examiner—John D. Yasko
Assistant Examiner—Adam J. Cermak
Attorney, Agent, or Firm—Townsend and Townsend

[57] ABSTRACT

A multiple pharmaceutical syringe (160), especially useful for use in dispensing insulin, includes a body (162) housing first and second pharmaceutical-filled cartridges (182, 184). The cartridges are of the type with a septum (190) at one end and a piston (224, 225) at the other end with the liquid pharmaceutical (226, 228) between the two. The body also defines an accumulator chamber (202) within which an accumulator piston (238) is slidably mounted. When the cartridges are mounted within the body, the septums are pierced by hollow spikes (188) which are connected to a flow path opening into the accumulator chamber. Check valves (230) are used at the distal ends of the spikes to prevent liquid flow back into the cartridges. Pressing on the cartridge pistons forces the liquids into the accumulator chamber. Once the desired amounts of both liquids are in the accumulator chamber, the needle assembly is mounted to the replaceable fluid path assembly which fluidly couples the needle to the accumulator chamber. The injection is given by driving the accumulators piston using the accumulator stem.

8 Claims, 22 Drawing Sheets

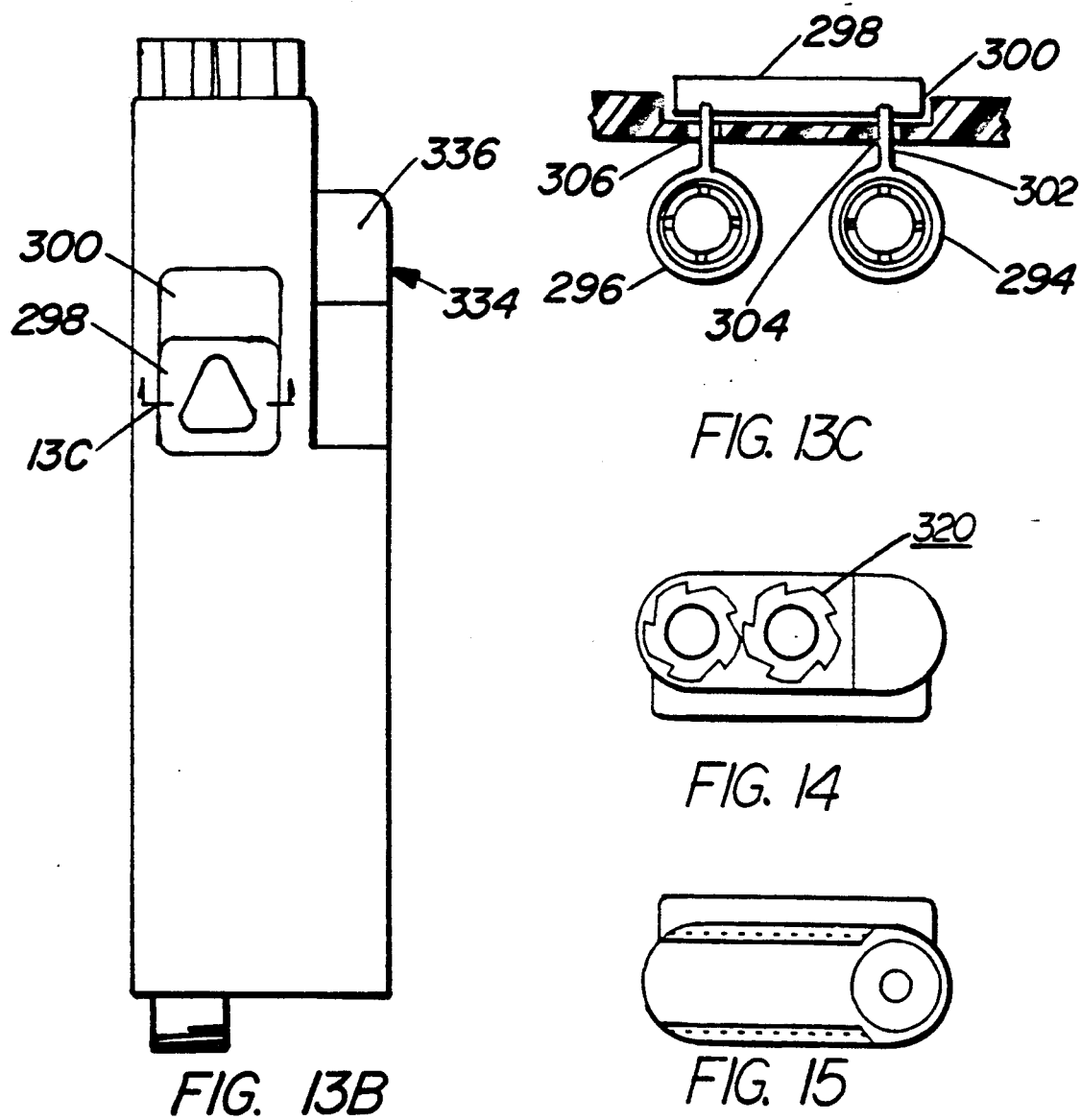

MULTIPLE PHARMACEUTICAL SYRINGE

CROSS REFERENCE TO RELATED APPLICATIONS

This is a continuation-in-part of both U.S. patent application Ser. No. 07/667,319, titled MULTIPLE CARTRIDGE SYRINGE, and U.S. patent application Ser. No. 07/668,278, titled MULTIPHARMACEUTICAL SYRINGE, both of which were filed on Mar. 8, 1991, the disclosures of which are incorporated by reference.

BACKGROUND OF THE INVENTION

Therapeutic insulin is of three basic types: fast-acting, intermediate-acting and long-acting. Insulin users often use a combination of two types of insulin depending on the user's blood sugar level, the time of day, nourishment intake, and expected activity. For example, insulin injected at the beginning of an active day may have more of the fast-acting insulin, while the insulin injection given at the end of the day before going to bed would likely have more intermediate- or long-acting insulin.

One of the problems with conventional insulin syringes is that they are designed to inject only one type of insulin, not a combination. Although insulin can be obtained as a mixture of the two types, the mixtures are generally a preset combination, such as 70% intermediate-acting and 30% fast-acting. Thus, the prior art limits the insulin user to a set mixture of the two insulins or the need to make two separate injections.

SUMMARY OF THE INVENTION

The present invention is directed to a syringe which preferably uses two or more conventional pharmaceutical cartridges to allow the user to deliver desired amounts and proportions of each during a single injection from a common accumulator chamber. This permits, for example, an insulin user to select the amounts and proportions of two types of insulin delivered with a single injection.

The multiple cartridge syringe includes a body housing first and second pharmaceutical-filled cartridges. The cartridges preferably are of the type with a septum at one end, an exposed piston at the other and the liquid pharmaceutical between the two. The body also houses an accumulator chamber within which an accumulator piston is slidably contained. In one embodiment the proximal end of the body is open to provide access to the three pistons by a single stem. In another embodiment the separate drive stems are used for each cartridge piston and for the accumulator piston. Their septums are each pierced by hollow spikes. The hollow spikes are connected to a flow path which opens into the distal end of the accumulator chamber. Check valves are preferably used, typically at the distal ends of the spikes, to allow the pharmaceutical within each cartridge to flow out of the cartridge through the spike but not the reverse.

Pressing on the piston within a cartridge causes the pharmaceutical within the cartridge to flow through the spike, through the check valve, along the flow path and into the accumulator chamber. The pressure and increasing volume of the liquid within the accumulator chamber forces the accumulator piston away from the distal end of the accumulator chamber towards the proximal end of the body. The cartridge pistons are each acted on until the desired amounts of both liquid pharmaceuticals have been forced into the accumulator chamber and mixed therein.

The needle assembly is then fluidly coupled to the accumulator chamber. In one embodiment this is accomplished by moving the needle assembly from its normally stored or retracted position to an extended position. This causes the distal end of the accumulator chamber to be fluidly coupled to the hollow needle. Pressing on the stem connected to the accumulator piston forces the newly-mixed liquids within the accumulator chamber through the hollow needle. Once the injection has been given, the needle assembly is moved back to its retracted position. This not only moves the needle to a safe position within the body, but also seals the needle from the accumulator chamber.

Preferably, a single stem is used to drive each of the pistons one-at-a-time. The stem can be retained by an end cap slidably mounted to the proximal end of the body. The end cap guides the stem as it pushes against the various pistons. After withdrawing the piston from the body, the end cap can be slid laterally to align the distal end of stem with a different piston.

A primary feature of the invention is that it permits a single injection of selected amounts and proportions of two or more liquid pharmaceuticals using a simple and compact syringe. In addition, the invention is designed to be usable with conventional pharmaceutical cartridges for reduced cost and enhanced flexibility. An insulin user is provided a flexible, convenient and compact syringe by which any desired proportion of insulins can be administered with a single injection.

Although the syringe as shown is a reusable design, it could easily be modified to be disposable by the user by preventing removal of the end cap and preventing removal of one or both of the spent pharmaceutical cartridges.

The accumulator piston can be made with a collapsible sterility skirt connected to the proximal end of the accumulator chamber. This will protect the sterility of the accumulator chamber during use and between uses.

The accumulator chamber is preferably sized to house substantially the entire stem or stems when the syringe is not being used. This, plus an in-line arrangement of the cartridges and the accumulator chamber, allows the syringe to be quite compact and yet a relatively sturdy package. The preferred configuration of the syringe reduces or eliminates the stigma of abnormality created by the use of conventional hypodermic syringes and pharmaceutical vials.

The invention can be carried out using structure by which check valves and flow paths connecting the interiors of the cartridges to the accumulator chamber and hollow needle is replaceable. This permits most of the syringe to be reusable, thus reducing cost for the user, while enhancing sterility. In a preferred embodiment, this is accomplished by mounting a replaceable fluid path cartridge to a body, the replaceable fluid path cartridge including the flow path elements from the spikes which pierce the septums on the cartridges through the accumulator chamber.

Another feature of the invention involves a provision of measured metering of the pharmaceuticals. This preferably accomplished using a preferably externally threaded stem driven by a hollow driver having internal threads at one end, the threaded driver being rotatable by the user. The threaded driver is preferably ratcheted and detented to provide audible and tactile indications of the amount of the pharmaceutical being dispensed from each cartridge. To reposition the threaded stem relative to the threaded driver, which is necessary when changing cartridges, a locking collar is preferably used to selectively secure the preferably externally threaded stem to the preferably internally threaded end of the driver. In this way, by moving the locking collar the threads can be disengaged to permit the threaded stem to be repositioned within the driver.

The present invention can also be carried out using a visually distinct display to visually indicate the movement of the plungers within the pharmaceutical cartridges, thus indicating the amount of pharmaceutical dispensed from each. This is preferably accomplished using a pick-up which senses the rotation of the threaded driver and advances a visual indicator, such as a continuous loop, in a manner which magnifies the movement of the piston. That is, if the piston moves 0.84 millimeter to dispense one unit of medicine, the indicator strip may move two or more times that distance. This magnification of distance is especially helpful for those users with poor eyesight. After one or more injections, the dosage indicator assembly can be reset by the user.

Other features and advantages of the invention will appear from the following description in which the preferred embodiments have been set forth in detail in conjunction with the accompanying drawings.

BRIEF DESCRIPTION OF THE DRAWINGS

FIGS. 13–15 are side, proximal end and distal end views of the syringe of FIG. 12 respectively, the accumulator chamber thumb driver shown pivoted to the use position in phantom in FIG. 13;

DETAILED DESCRIPTION OF THE PREFERRED EMBODIMENTS

Figure 1:
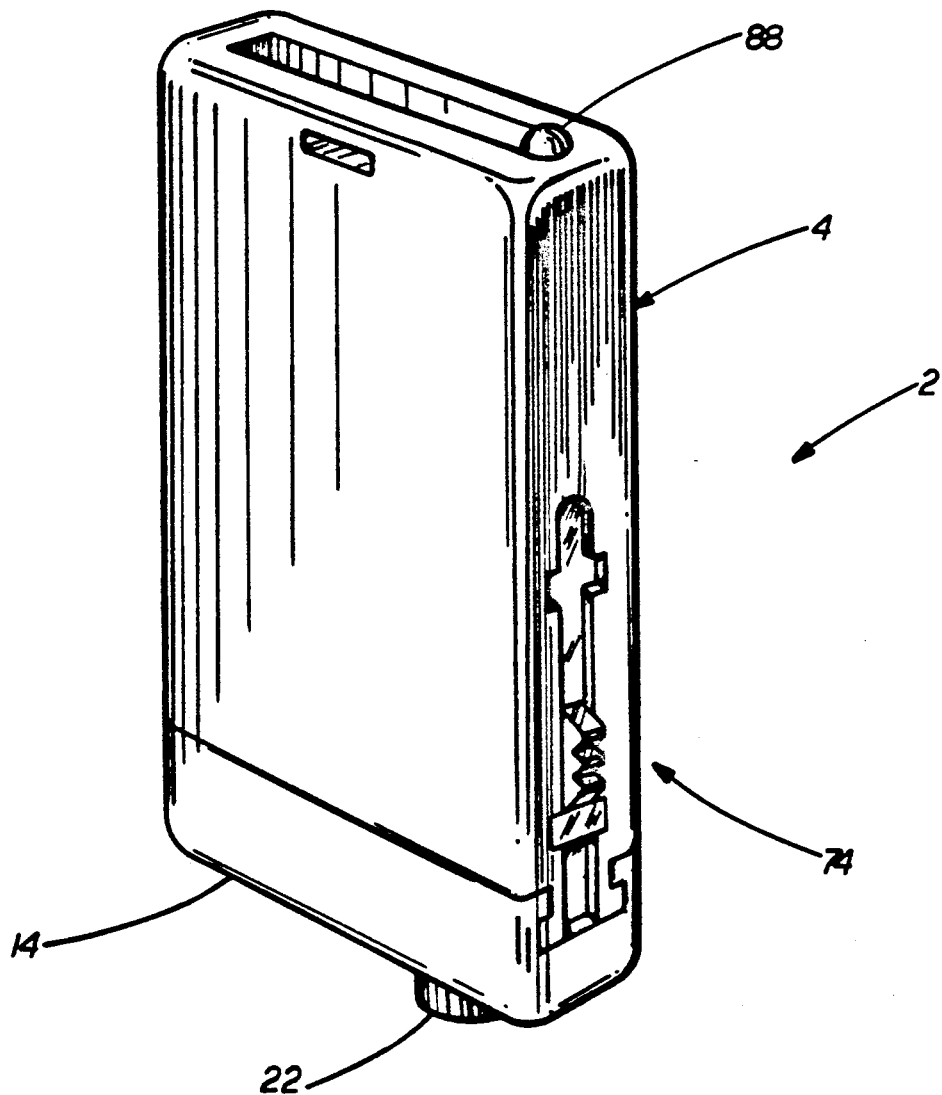
FIG. 1 is an isometric view of a syringe made according to the invention.
Figure 2:
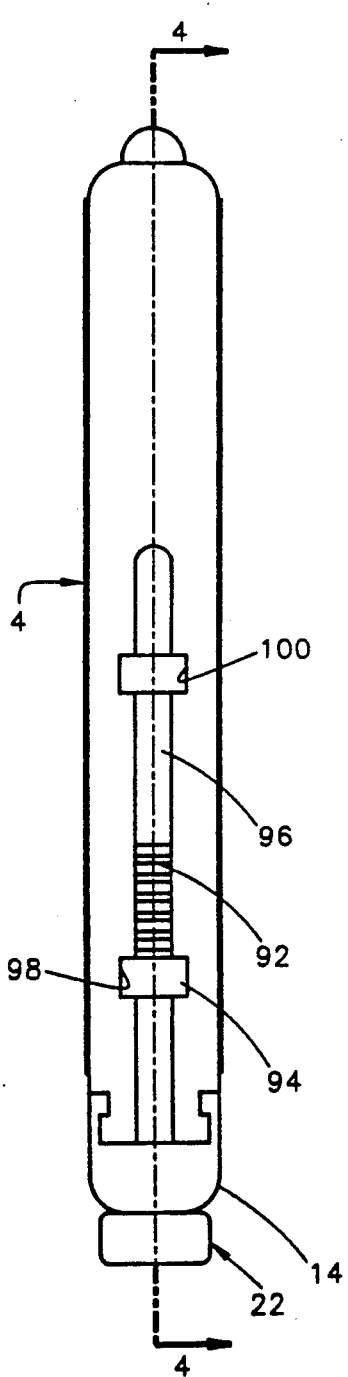
FIG. 2 is a side view thereof showing the position control button of the needle assembly.
Figure 3:
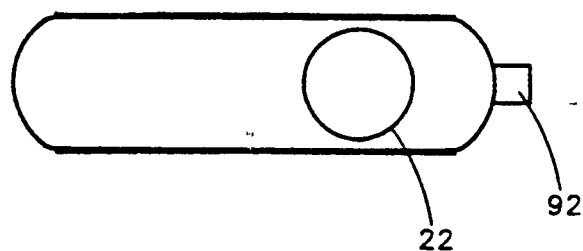
FIG. 3 is an end view thereof showing the finger engagement surface of the stem.
Figure 4:
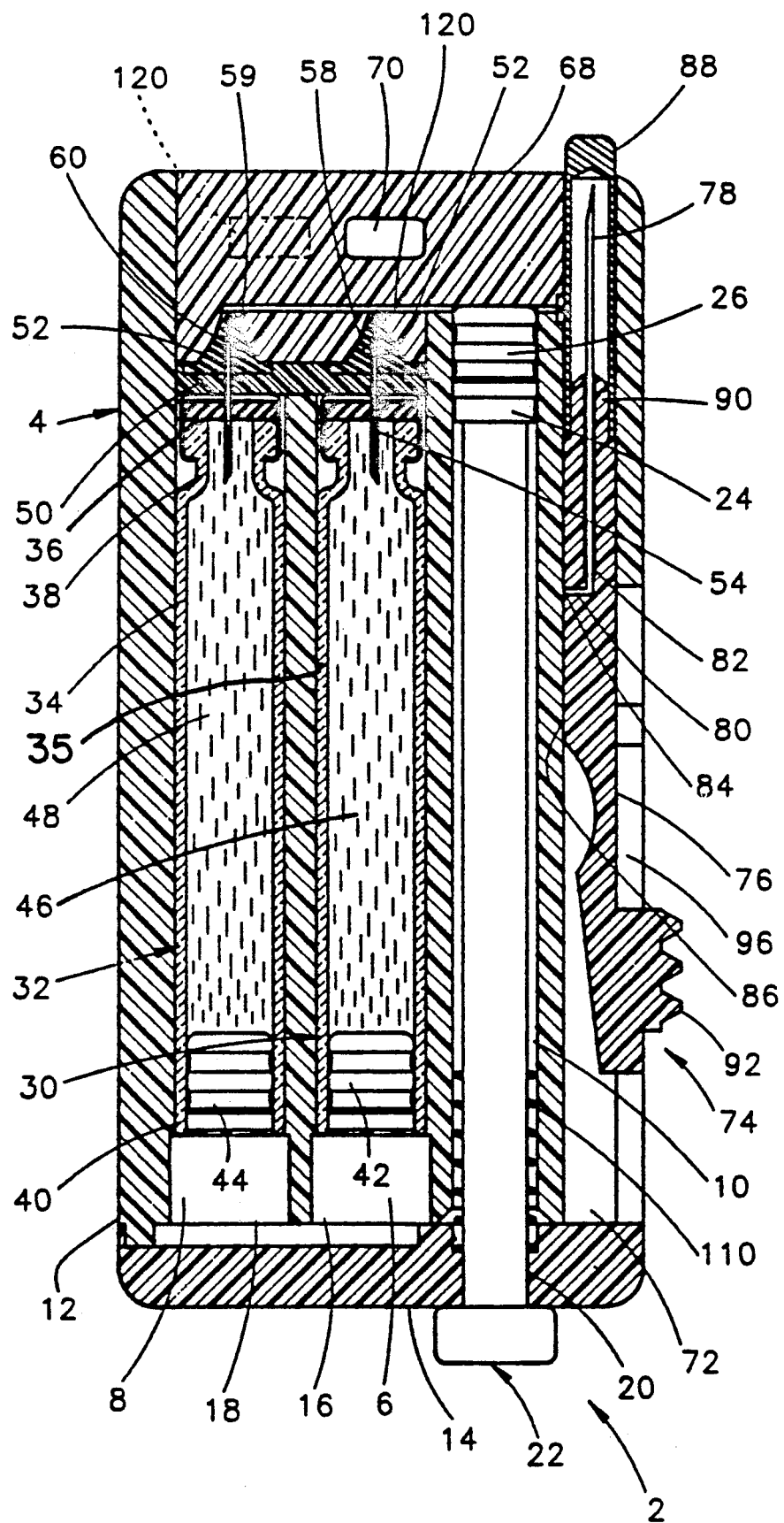
FIG. 4 is a cross-sectional view taken along line 4—4 of FIG. 2.

Referring the reader to FIGS. 1–3, a multiple cartridge syringe 2 is shown to include a body 4 defining first and second chambers 6, 8 and an accumulator chamber 10. Body 4 is made of a clear, pharmaceutically compatible plastic, such as polypropylene or acrylic. A proximal end 12 of body 4 is covered by a sliding end cap 14, thus covering the opened proximal ends 16, 18 of chambers 6, 8. End cap 14 has an opening 20 through which a stem 22 passes. As shown in FIG. 4, the distal end 24 of stem 22 is normally positioned adjacent a piston 26 mounted within accumulator chamber 10 at a distal end 28, see FIG. 5, of chamber 10.

Chambers 6, 8 are sized for receipt of first and second conventional pharmaceutical cartridges 30, 32. Cartridges 30, 32 each include a barrel 34, 35 having a pierceable septum 36 at a far end 38 and an opened near end 40. First and second cartridges 6, 8 include first and second pistons 42, 44 and contain first and second liquid pharmaceuticals 46, 48 between septums 36 and pistons 42, 44.

Figure 7:
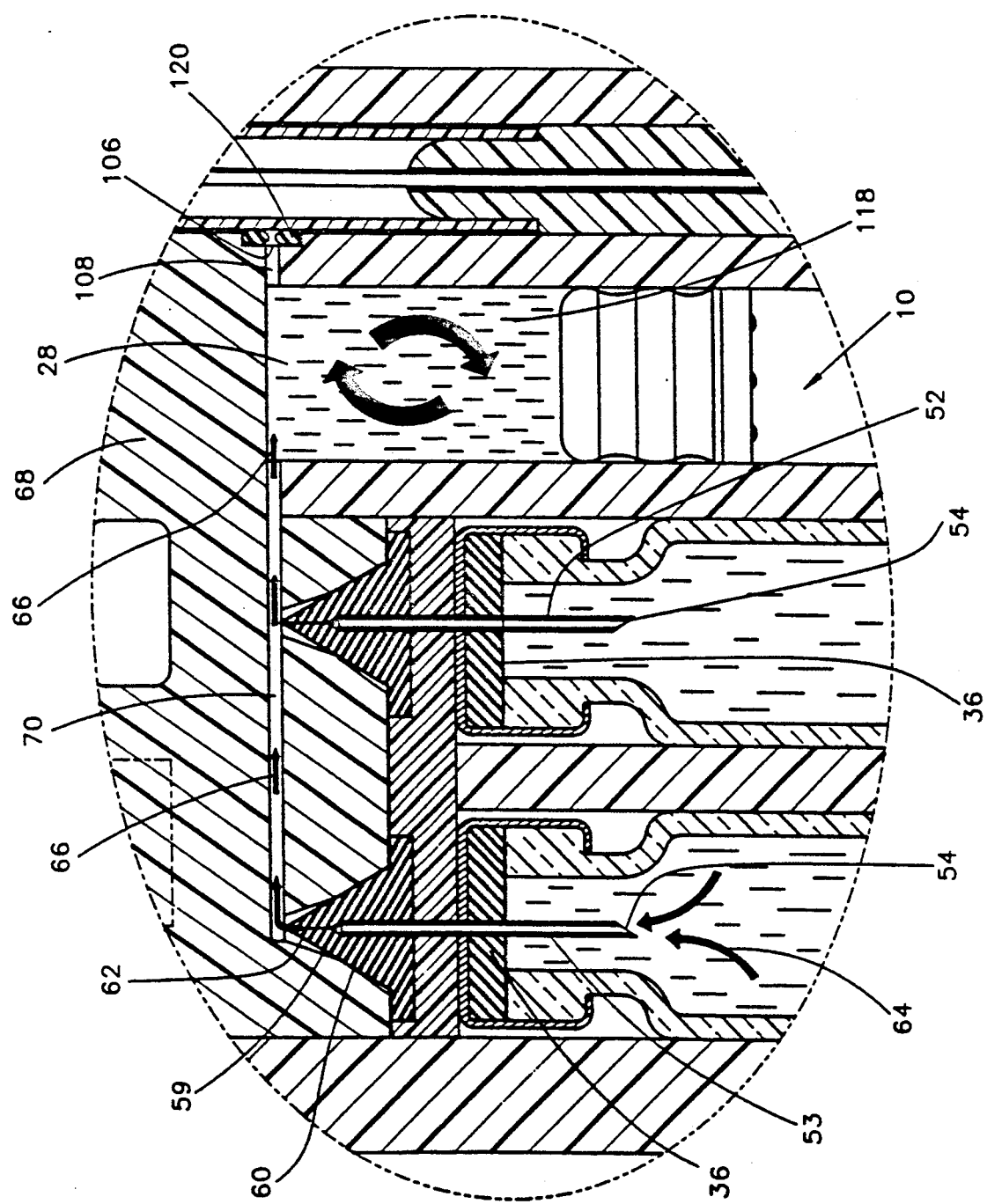
FIG. 7 is an enlarged view of a portion of the syringe of FIG. 6 taken along line 7—7.

The far ends 38 of first and second cartridges 30, 32 rest against a check valve support plate 50. Hollow spikes 52, 53 (see FIG. 7) are mounted to and pass through support plate 50. Spikes 52, 53 have sharpened ends 54 which pierce septums 36 when cartridges 30, 32 are inserted into first and second chambers 6, 8. Slit conical check valves 58, 59, shown best in FIG. 7, are mounted to the outer ends 60 of spikes 52. Check valves 58, 59 have slits 62 which permit fluid to flow in the direction of arrows 64, 66 but not in the reverse direction. Valves 58 are preferably made of a firm elastomeric material, such as silicone rubber, such as sold by Dow Chemical Company of Midland, Mich. as Q4765.

Support plate 50 and check valves 58, 59 are retained in position by an end cap 68 permanently mounted to housing 4, such as with an adhesive. End cap 68 has a flow path 70 which provides fluid communication between the two check valves 58, 59 and distal end 28 of accumulator chamber 10.

Body 4 also includes a guide slot 72 having a rectangular cross-sectional shape. A needle assembly 74 is mounted for slidable movement within guide slot 72 and includes a needle carrier 76 to which a hollow needle 78 is mounted. An L-shaped bore 80 is formed in needle carrier 76 to connect the proximal end 82 of needle 78 to an orifice 84 along a flat side 86 of carrier 76. Needle assembly 74 also includes protective sheath 88 which is removably mounted to the outer end 90 of needle carrier 76 so to protect against contamination of needle 78 and inadvertent injury by the needle.

Figure 8:
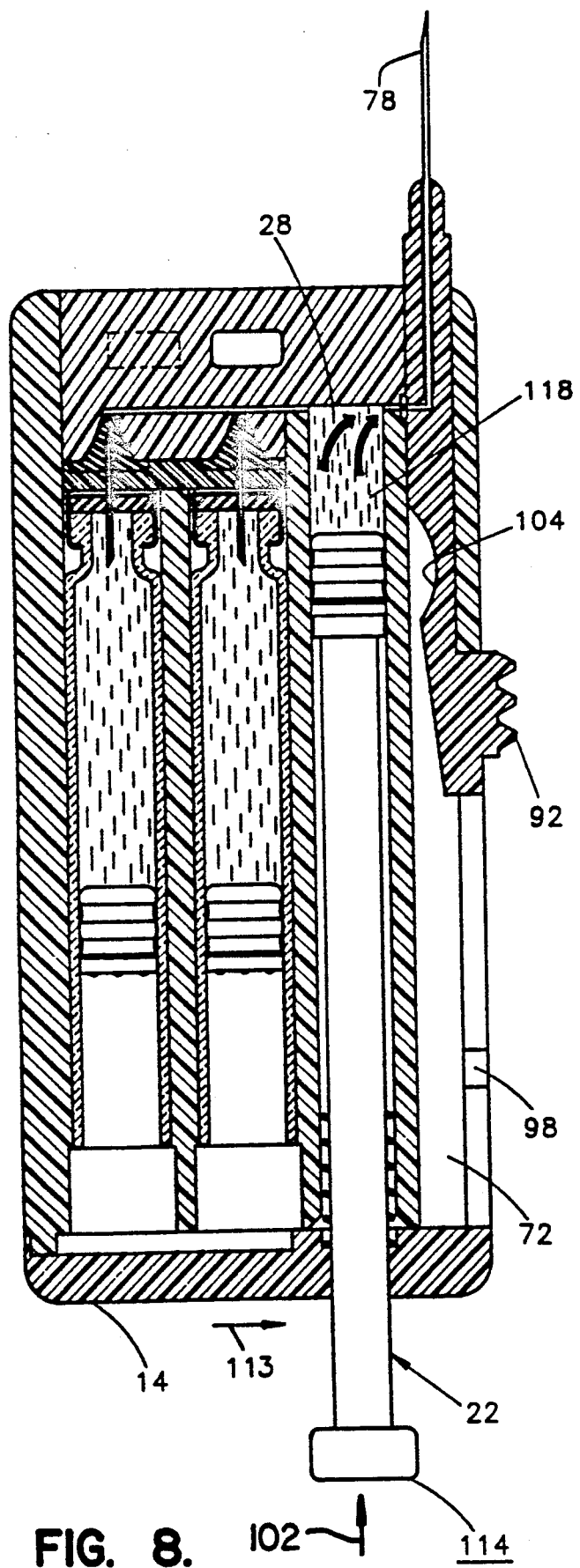
FIG. 8 shows the syringe of FIG. 6 with the end cap shifted back to the position of FIG. 4, the needle assembly in its extended position with the needle sheath removed, and the stem beginning to drive the accumulator piston to force the mixed liquid out of the accumulator chamber and through the hollow needle.
Figure 9:
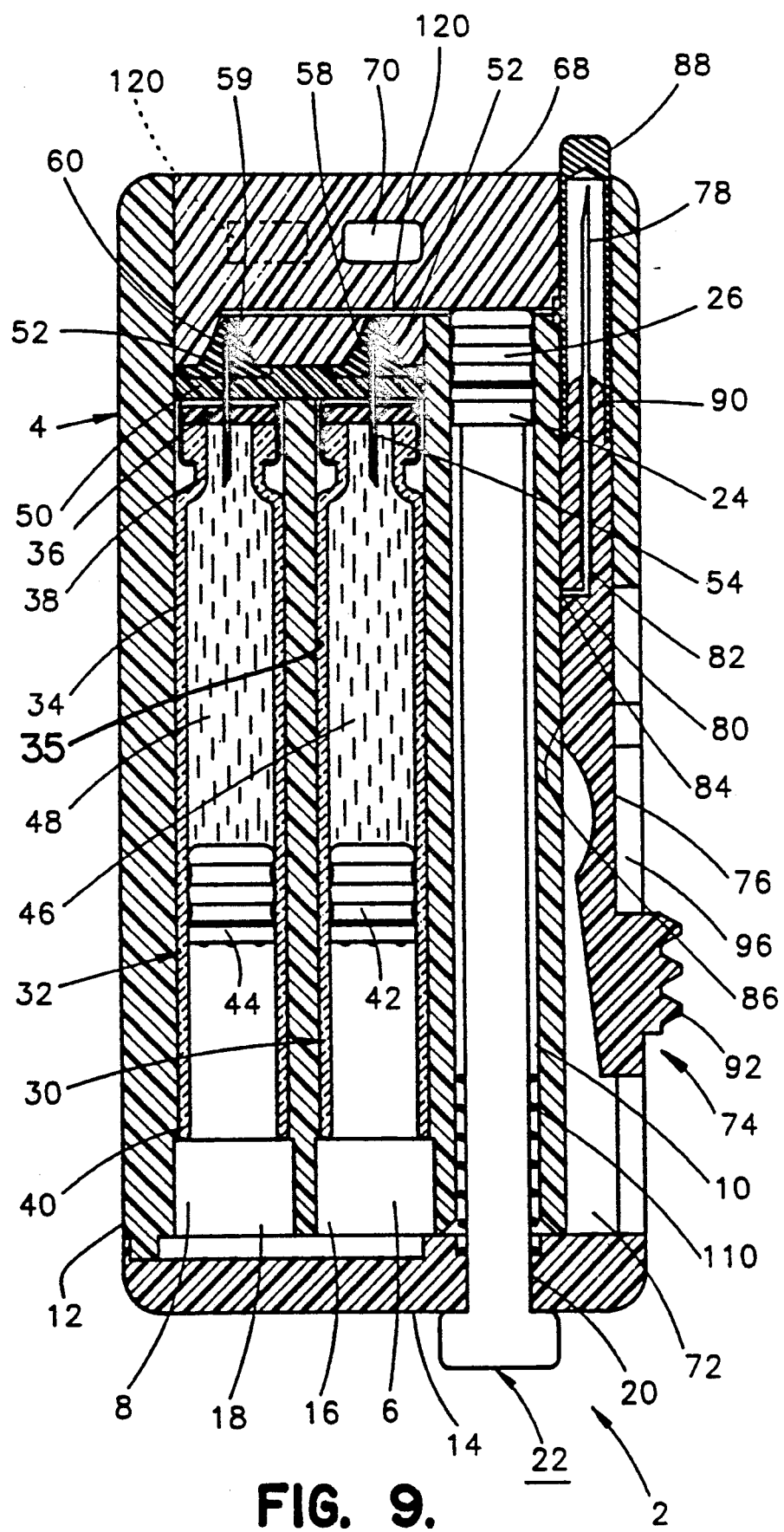
FIG. 9 shows the syringe of FIG. 8 following an injection with the needle assembly in the retracted position.

Needle carrier 76 includes a push button 92 having an enlarged end 94, see FIG. 2. Push button 92 is sized to move along a slot 96 while enlarged end 94 is sized to engage enlarged sections 98, 100 of slot 96. To move enlarged end 94 from enlarged section 98, as shown in FIGS. 2 and 4, to enlarged section 100, shown in FIG. 8, the user presses down upon push button 92 and slides needle assembly 74 in the direction of arrow 102 as shown in FIG. 8. An appropriate resilience is provided to needle carrier 76 by a cross-sectional decrease at 104 in the needle carrier. With needle carrier 76 in the extended position of FIG. 8, orifice 84, which opens into L-shaped bore 80, is aligned with an end 106 of a bore 108 (see FIG. 7), thus fluidly coupling distal end 28 of accumulator chamber 10 to hollow needle 78.

Figure 5:
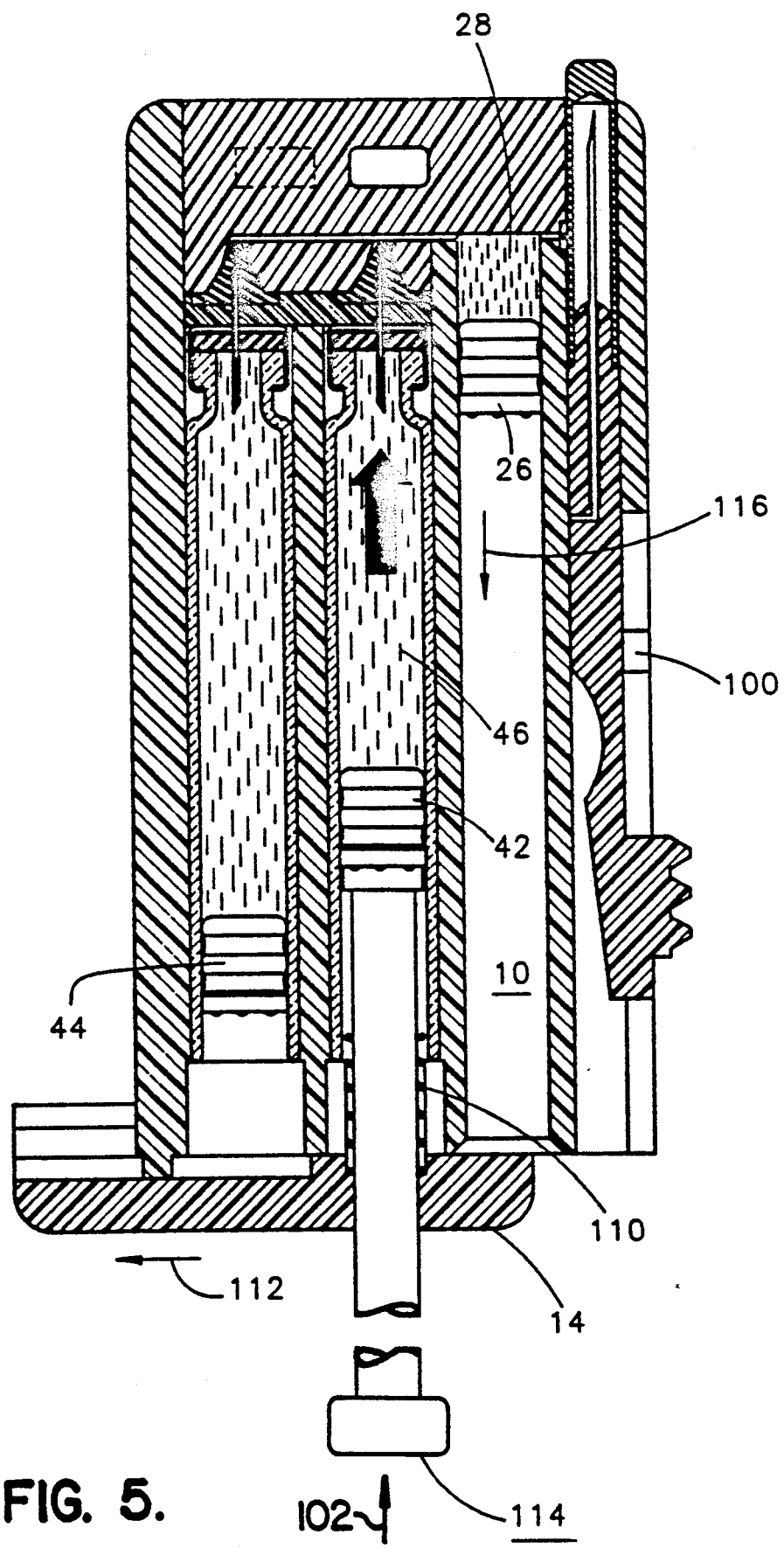
FIG. 5 is a cross-sectional view of the syringe of FIG. 4 with the end cap shifted and the plunger driving the first piston of the first cartridge forcing the first liquid into the accumulator chamber.

To move stem 22 from the position of FIG. 4 to the position of FIG. 5, the user first withdraws stem 22 as far as possible from accumulator chamber 10. During the final movement of stem 22 from chamber 10, a coil spring 110 is compressed. End cap 14 is then moved in the direction of arrow 112. After stem 22 is no longer aligned with accumulator chamber 10, the user can release stem 22. Once stem 22 becomes aligned with first chamber 6, spring 110 automatically forces stem 22 into the first chamber, thus aiding proper axial alignment. The user then presses against the outer finger engaging surface 114 of stem 22 forcing first piston 42 in the direction of arrow 102. This causes first liquid 46 to flow through spike 52, check valve 58, flow path 70, and into distal end 28 of accumulator chamber 10. The fluid pressure of liquid 46 within chamber 10 causes accumulator piston 26 to move in the direction of arrow 116. Liquid 46 is not forced into second cartridge 32 due to the use of check valve 59.

Figure 6:
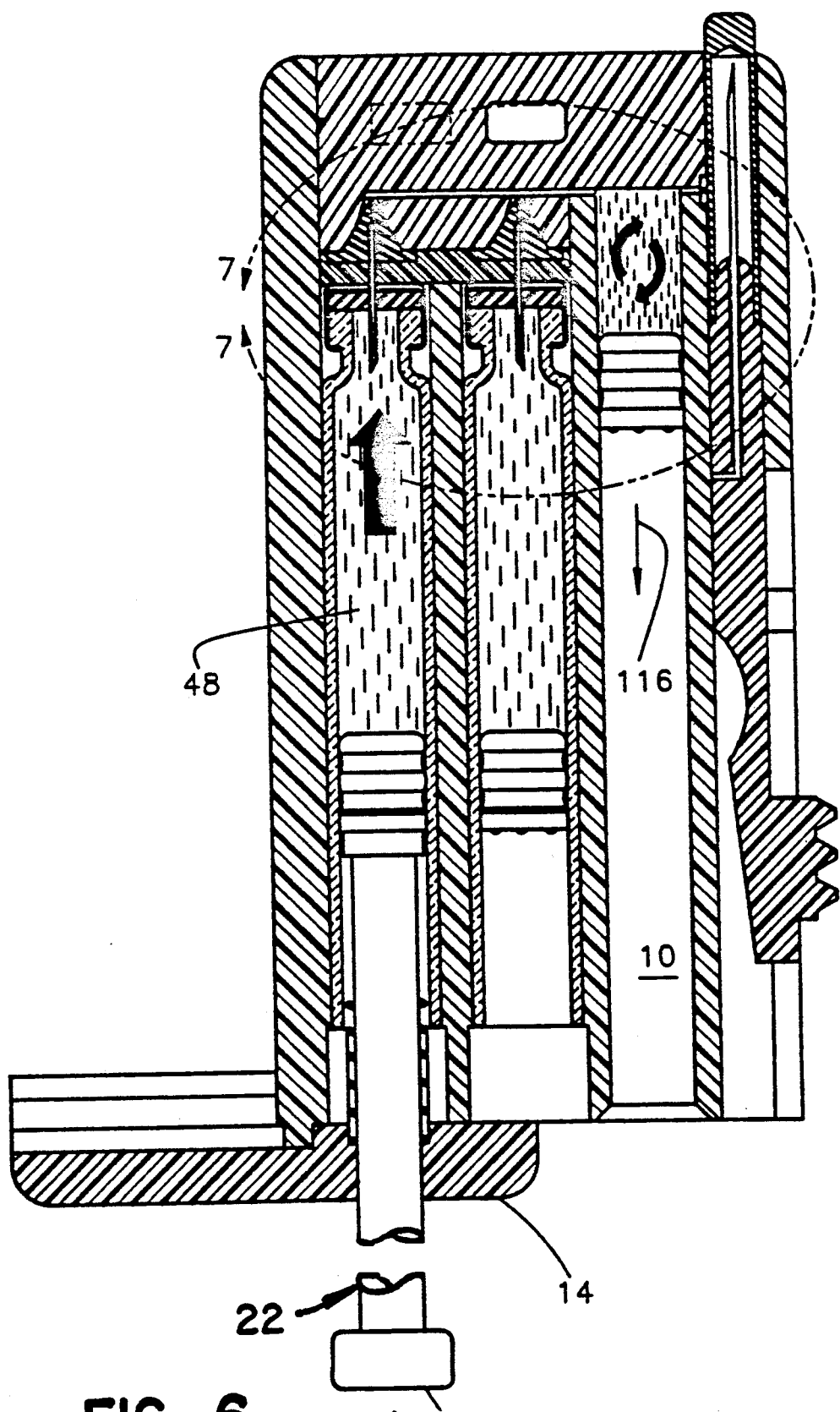
FIG. 6 shows the syringe of FIG. 5 with the end cap shifted to another position and the stem engaging the second piston of the second cartridge forcing the second liquid into the accumulator chamber where it mixes with the first liquid.

After a sufficient amount of liquid 46 has been introduced into distal end 28 of chamber 10, stem 22 is then again withdrawn and cap 14 is again slid in the direction of arrow 112 until stem 22 becomes aligned with second chamber 8. The above process is repeated for second liquid 48 as shown in FIGS. 6 and 7 to create a mixed liquid 118 in distal end 28 of accumulator chamber 10.

Stem 22 is then withdrawn from second chamber 8 and end cap 14 is moved in direction of arrow 113 to the position of FIG. 8. Push button 92 is then depressed and needle assembly 74 is driven from the position of FIG. 6 to the position of FIG. 8. Protective sheath 88 is then removed and one end of the sheath is inserted into a blind storage hole 120 formed in end cap 68. The injection is given by pressing on surface 114 of stem 22 which causes the mixed liquid 118 to flow through bore 108, bore 80 and hollow needle 78.

Figures 10A, 10B:
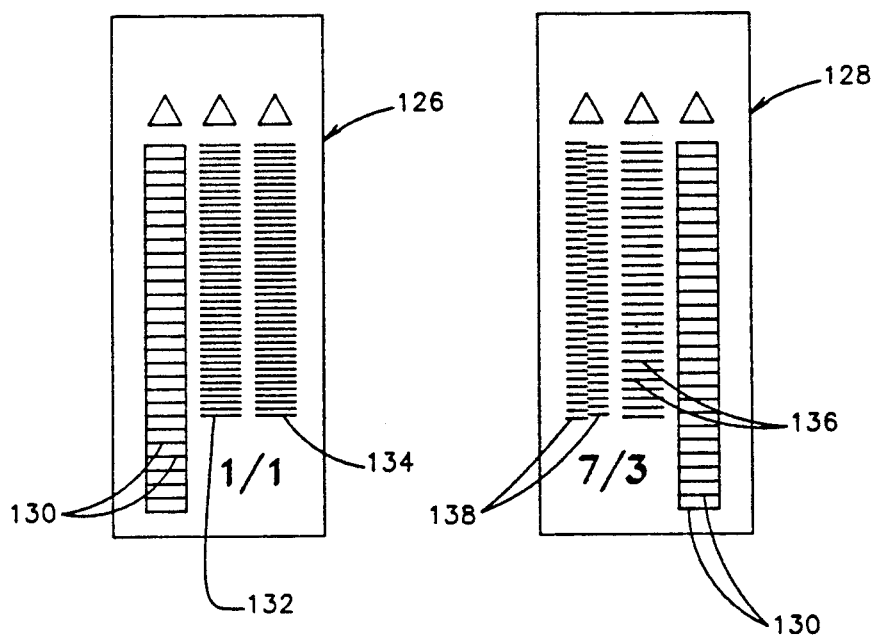
FIGS. 10A and 10B are front views of transparent dosage labels.

The amount of liquids 46, 48 forced into distal end 28 of accumulator chamber 10 can be gauged through the use of transparent dosage labels 126, 128 shown in FIGS. 10A and 10B. Label 126 includes accumulator calibrations 130. Labels 126, 128 are transparent except for the markings shown in FIGS. 10A and 10B to provide an unimpeded view of the contents of cartridges 30, 32 and accumulator chamber 10. The space between each calibration 130 equals one unit of medication. Label 126 also include first and second pharmaceutical calibrations 132, 134. Calibrations 132, 134 are each spaced apart by distances equal to one-half of a unit of medicine. Therefore, if the user moves pistons 42, 44 from one calibration 132, 134 to the next calibration 132, 134, equal amounts (one-half unit each) of liquids 46, 48 will be forced into accumulator chamber 10 to move piston 26 a distance equal to the distance between successive calibrations 130.

Label 128, mounted to the opposite side of body 4 as label 126, is used when the proportion of first liquid 46 to second liquid 48 is 7 to 3. The distance between successive first and second pharmaceutical calibrations 136, 138 corresponds to 70% of a unit and 30% of a unit respectively. Note that successive calibrations 138 are staggered - otherwise they could be too close together for easy reading. Labels 126, 128 are preferably removable so that labels having other calibrations for other mixture can be used as well.

Once the injection is complete, sheath 88 is removed from hole 120 and safely replaced over needle 78, button 92 is depressed to disengage enlarged end 94 from enlarged section 100, and needle 74 is brought back to its retracted position of FIGS. 4–6. Releasing push button 92 permits large end 94 to once again engage enlarged section 98 to keep the needle assembly from inadvertently being extended.

A fluid seal is provided at end 106 of bore 108 by an O-ring 124 as shown in FIG. 7. O-ring 124 engages the outer surface of sheath 88 when needle assembly 74 is in its retracted position of FIGS. 4–6 and presses against flat side 86 of needle carrier 76 in the region surrounding position 84 and the end of L-shaped bore 80 when in the extended position of FIG. 8. Instead of using a separate O-ring, other types of seals, including a molded-in, outwardly extending ring seal, could be used. Also, to aid sterility, a check valve can be used adjacent O-ring 124; this can be especially useful when a removable needle assembly is used.

The advantage of using blind hole 120 to temporarily house sheath 88 causes the sheath to extend laterally outwardly from the syringe during use. Thus, if the user inadvertently forgets to replace the sheath before withdrawing needle assembly back into guide slot 72, sheath 88 will immediately get in the way when the user attempts to store the syringe in the user's pocket, purse or carrying pouch. Also, if safety sheath 88 is not in place when pistons 42, 44 are depressed, liquid may leak through bore 108 and out guide slot 72. Thus, the user has an additional reason for properly maintaining safety sheath 88 in place.

For the convenience of the user, a through hole 122 can be provided through end cap 68 to permit syringe 2 to be carried, for example, on a keychain.

Figures 11A, 11B:
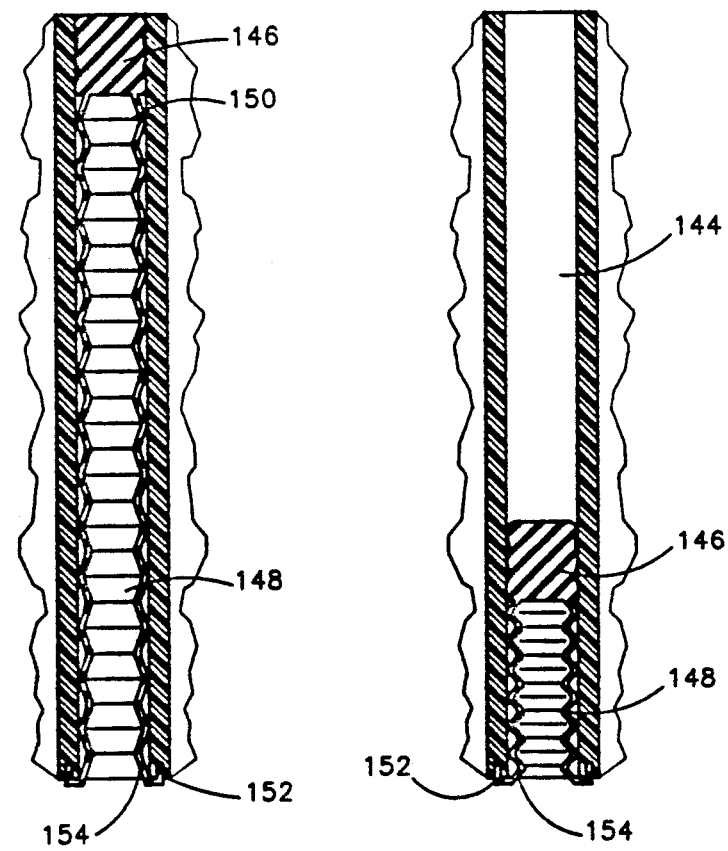
FIGS. 11A and 11B are simplified views showing the accumulator piston and chamber of FIGS. 4 and 5 used with a sterility skirt.

FIGS. 11A and 11B illustrate, in schematic form, an accumulator chamber 144 housing an accumulator piston 146 and a sterility skirt 148. Skirt 148 is a lightweight, fluid impervious, flexible tubular material, such as silicone rubber, secured to piston 146 at one end 150 of skirt 148 and to the proximal end 152 of chamber 144 at the other end 154 of skirt 48. Skirt 148 is in its extended condition of FIG. 11A when piston 146 is fully within chamber 144 and in its compressed condition of FIG. 11B when piston 146 is near proximal end 152. Therefore, skirt 148 and piston 146 to help keep the inner walls of chamber 144 sterile during use and between uses. Other methods for insuring sterility is maintained can be used as well.

FIGS. 12-16 illustrate a further embodiment of the invention. Syringe 160 includes a body 162 defining first, second and third chambers 164, 166, 168. Chambers 164, 166 are separated into distal ends 170, 172 and proximal ends 174, 176 by annular shoulders 178, 180. Distal ends 170, 172 are sized for receipt of first and second pharmaceutical cartridges 182, 184, cartridge 182 having a larger diameter and a larger volume than cartridge 184, typically 3 ml versus 1½ ml. Cartridges 182, 184 are secured to a manifold base and accumulator chamber assembly 186. See FIG. 17. Assembly 186 includes sharpened hollow spikes 188 used to pierce the septums 190 of cartridges 182, 184. Cartridges 182, 184 are secured to assembly 186 through the engagement of projections 192 extending inwardly from clips 194, four of which surround each spike 188, with a proximally facing edge 196 of a collar 198. Assembly 186 also includes a portion 200 defining an accumulator chamber 202, portion 200 fitting within third chamber 168 of body 162.

Figure 18:
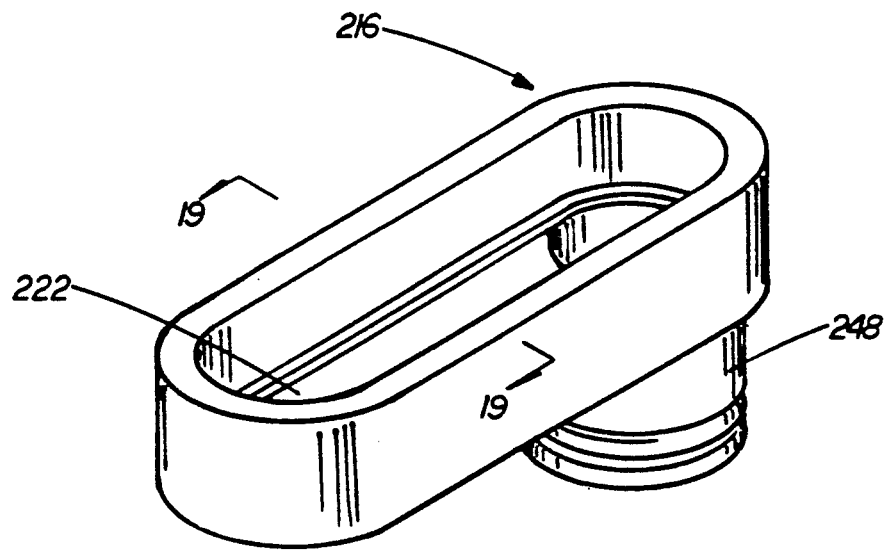
FIG. 18 is an isometric view of the manifold cover of FIG. 16.
Figure 19:
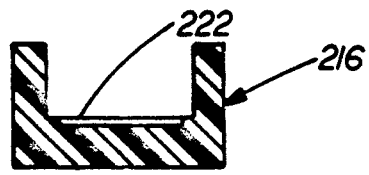
FIG. 19 is a cross-sectional view taken along line 19—19 of FIG. 18 with the depth of the channel exaggerated for purposes of illustration.
Figure 20:
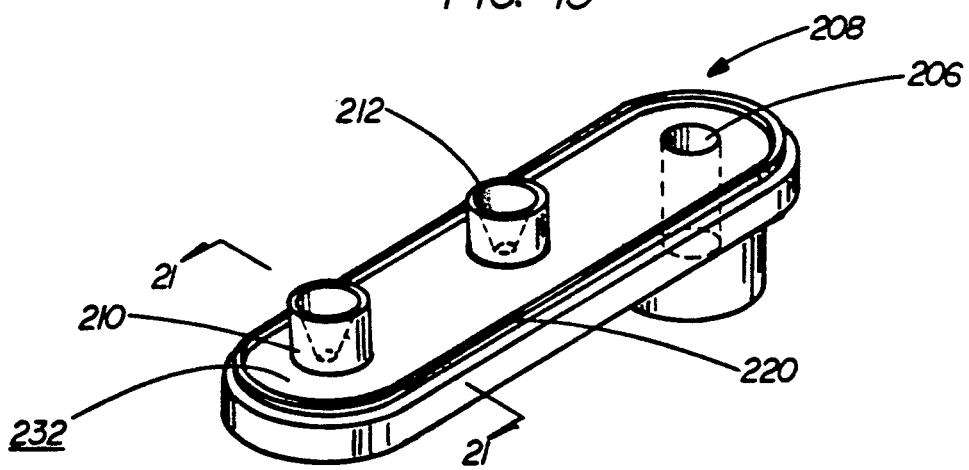
FIG. 20 is an isometric view of the manifold check valve of FIG. 16.
Figure 21:
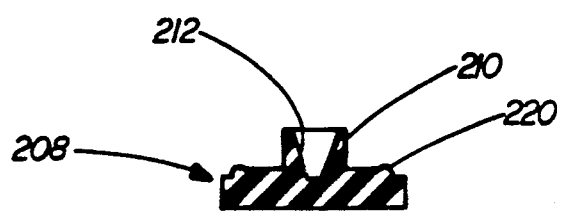
FIG. 21 is a cross-sectional view taken along line 21—21 of FIG. 20.
Figure 23:
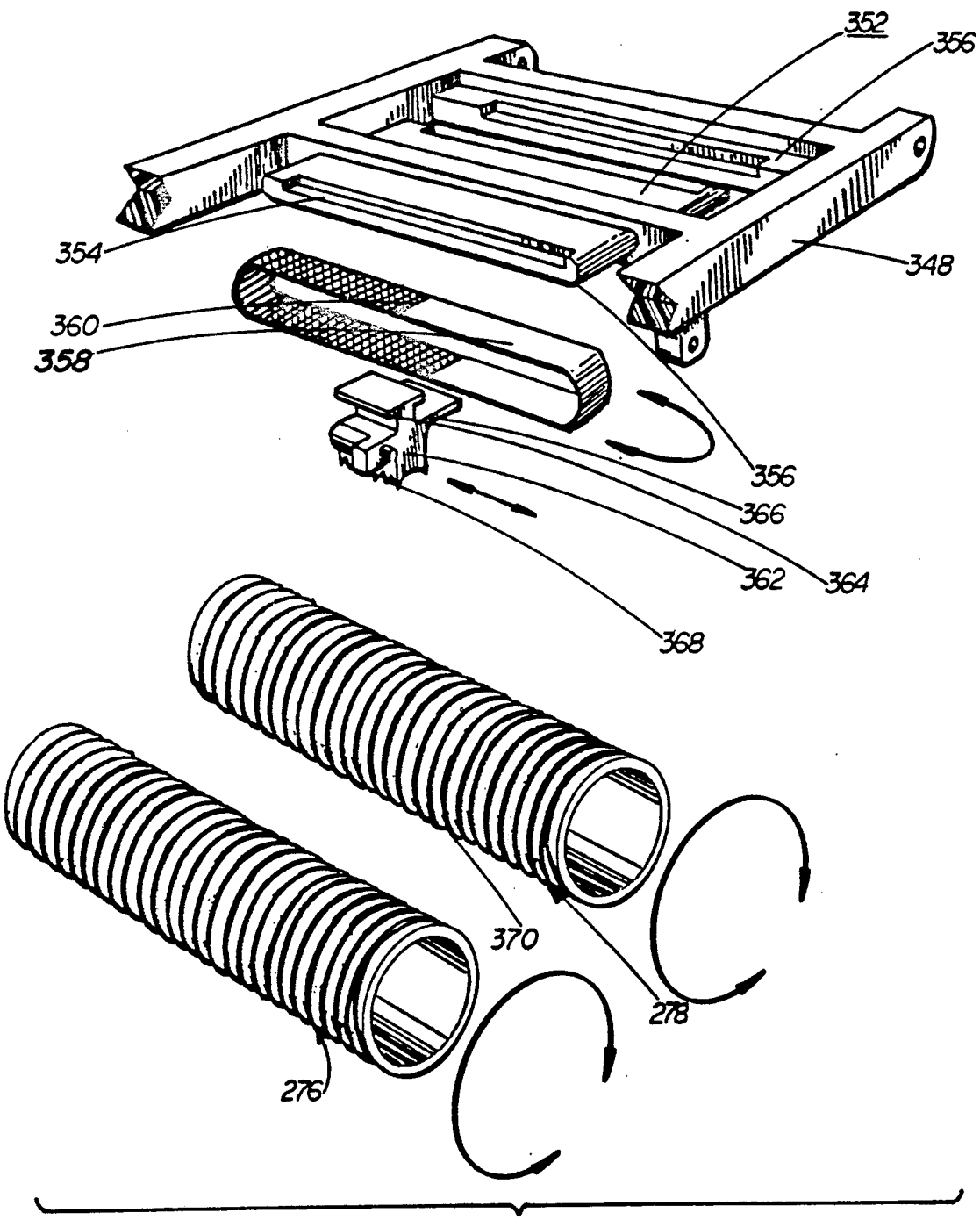
FIG. 23 is a simplified exploded isometric view of a portion of the optical dose indicator of FIG. 13A together with associated stem drivers.
Figure 24:
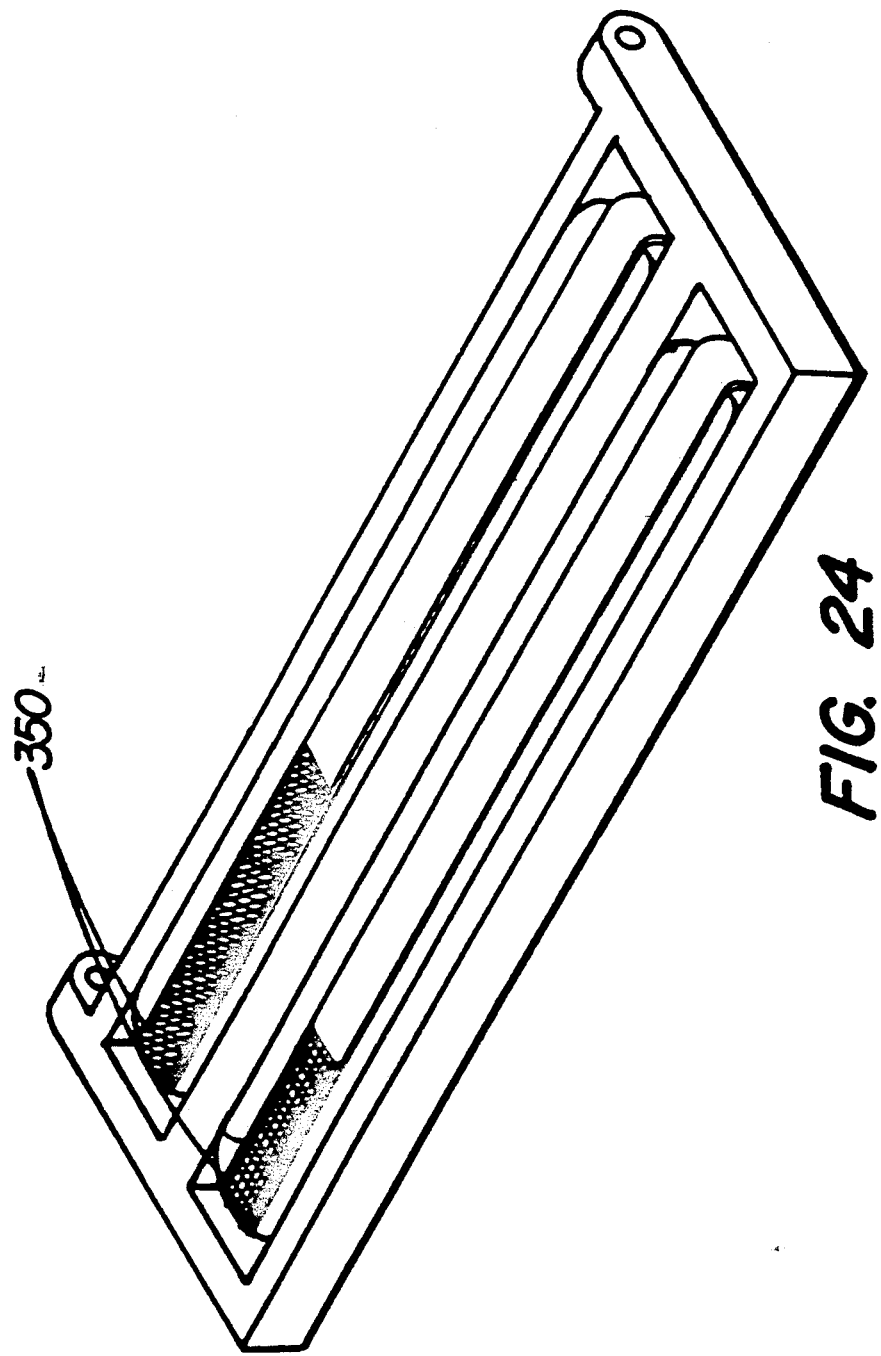
FIG. 24 shows the frame, indicator ribbons and followers of FIG. 23 in an assembled condition.
Figure 25:
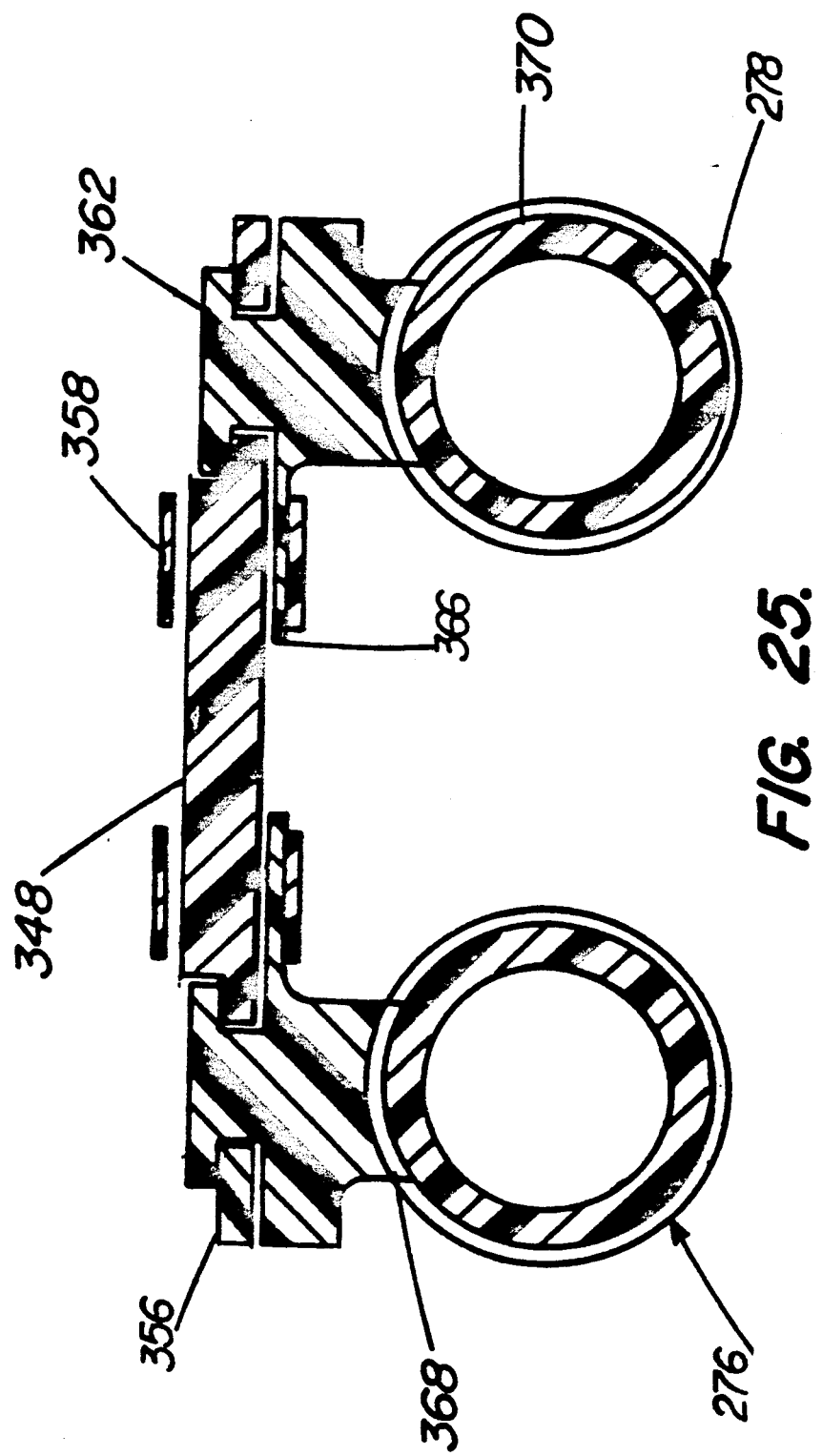
FIG. 25 is a simplified cross-sectional view showing the structure of FIG. 24 engaging associated stem drivers.

Assembly 186 includes a cylindrical extension 204 which fits snugly within a complementarily shaped blind bore formed within an elastomeric manifold check valve 208. See FIGS. 18 and 19. Check valve 208 is preferably of a 50 durometer rubber, such as silicone rubber, and includes a pair of extensions 210 each having a cylindrical outer surface and a conical inner surface 212. Extensions 210 are sized for complementary mating engagement within tapered openings 214 formed within assembly 186. When assembly 186 and manifold check valve 208 are assembled, extensions 210 engage tapered openings 214 to act as check valves while cylindrical extension 204 fits snugly within blind bore 206.

Figure 12:
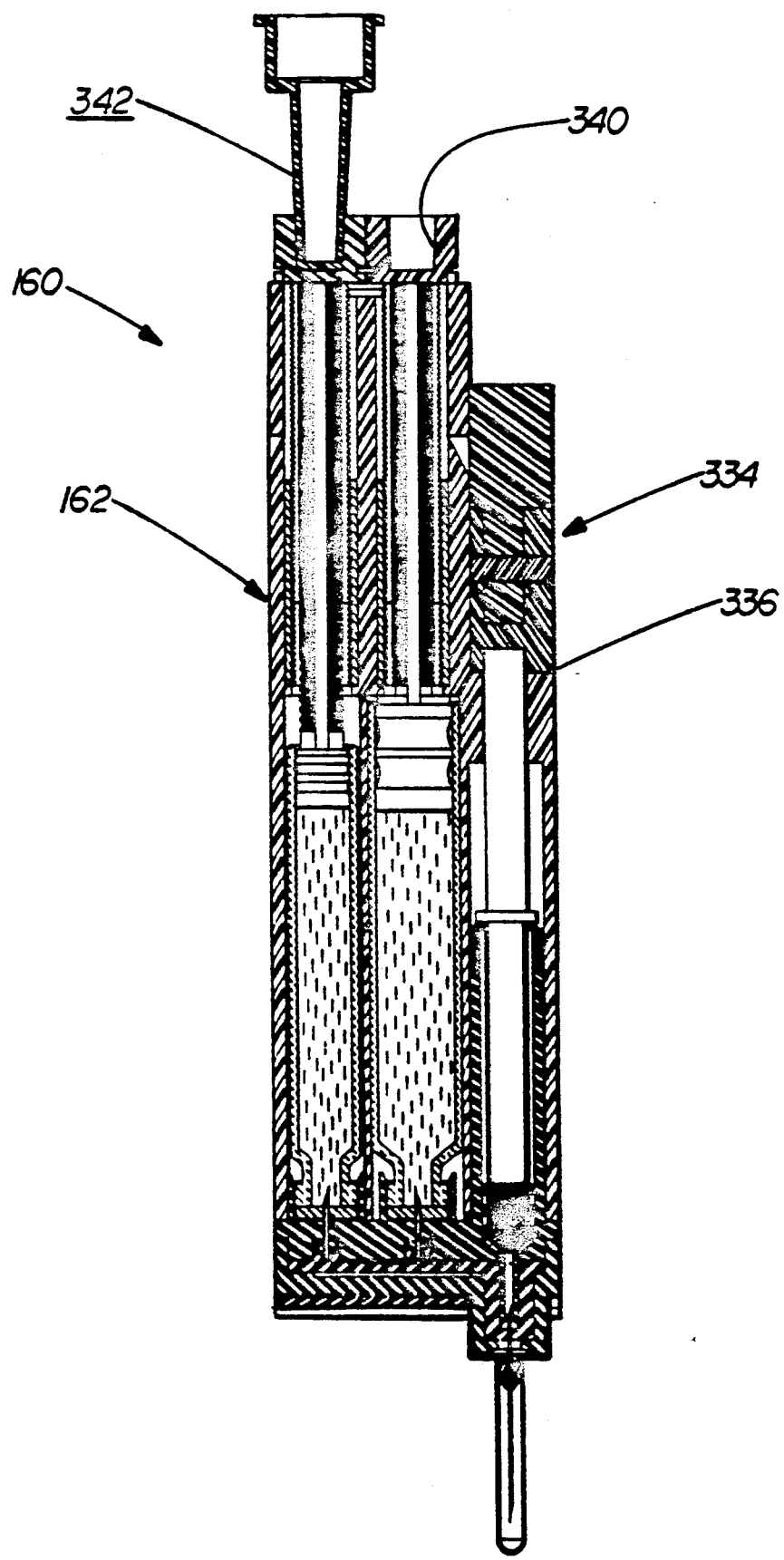
FIG. 12 is a cross-sectional view of an alternative embodiment of the syringe of FIG. 4 shown in the pre-use condition.
Figure 12A:
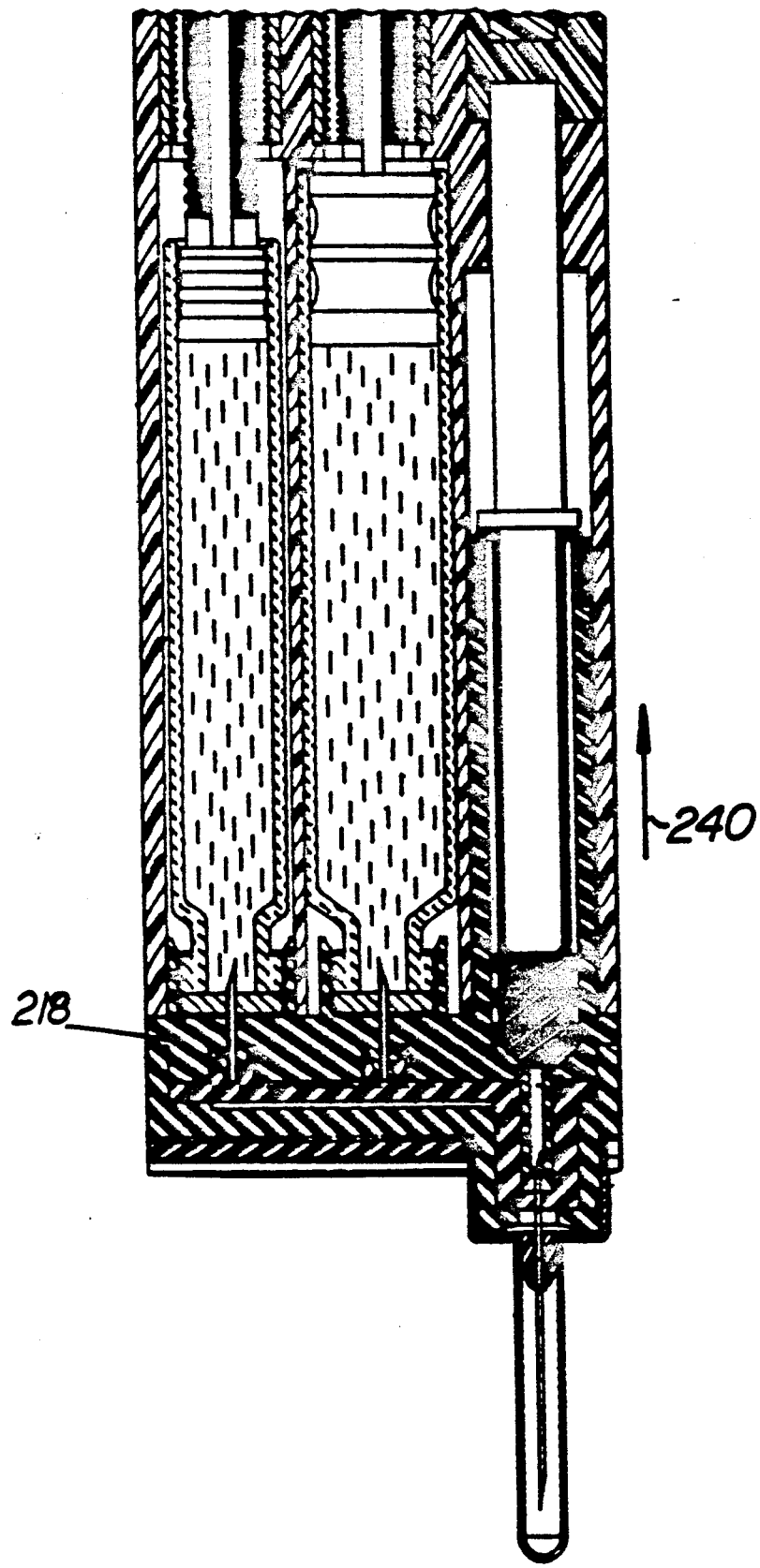
FIG. 12A is an enlarged view of the outer or distal end of the syringe of FIG. 12.
Figure 12B:
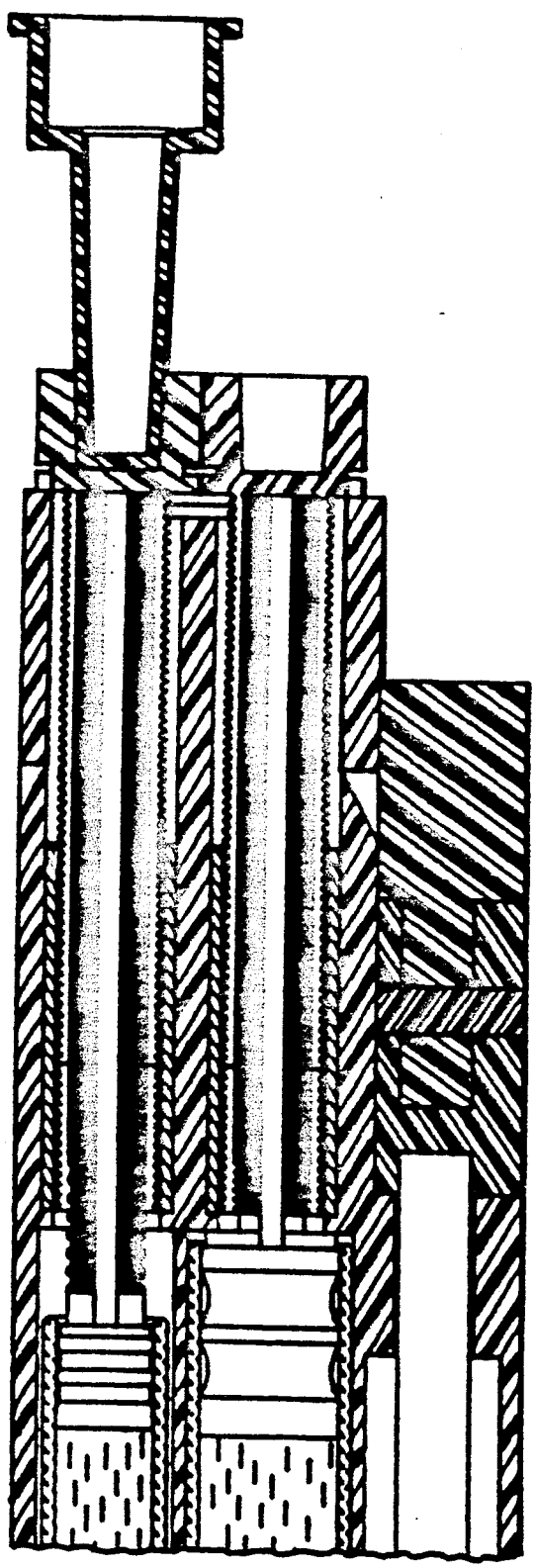
FIG. 12B is an enlarged view of the near or proximal end of the syringe of FIG. 12.
Figure 22:
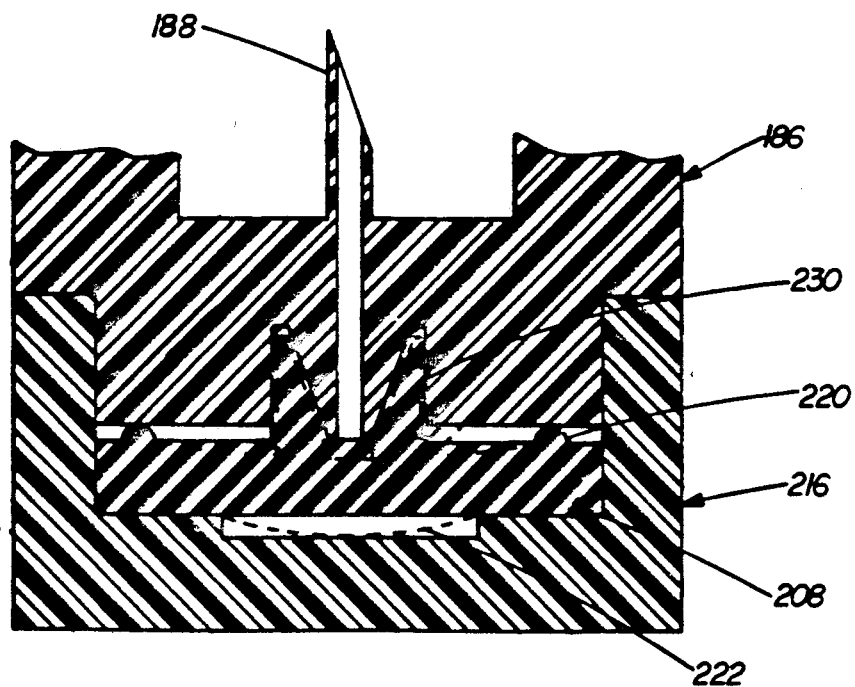
FIG. 22 is an enlarged cross-sectional view showing the replaceable fluid path cartridge of FIG. 12 and illustrating, in exaggerated form, the movement of the manifold check valve from its solid line position of FIGS. 12 and 12A to a dashed line position, thus opening up a fluid pathway between the interior of the associated cartridge and the accumulator chamber.

A manifold cover 216 is secured to assembly 186 along their intersecting surfaces 218, see FIG. 12A, using an adhesive or ultrasonic welding techniques. Doing so securely captures manifold check valve 208 between assembly 186 and manifold cover 216 so that a perimeter ring seal 220 formed on manifold check valve 208 provides a tight seal against assembly 186. Cover 216 includes a channel 222, typically 3.2 mm. wide and 0.38 mm. deep. Channel 222 permits manifold check valve 208 to deflect into the channel, as shown in dashed lines in FIG. 22, when one of the pistons 224, 225 of cartridges 182, 184 are driven along the length of the cartridges to force one of the liquid pharmaceuticals 226, 228 past the structures 210, 214 which form a check valve 230. The liquid pharmaceutical then flows between a surface 232 of manifold check valve 208 and a surface 234 of assembly 186, between cylindrical extension 204 and blind bore 206, through the bore 236 formed in extension 204 and into accumulator chamber 202. This causes accumulator piston 238 to move in the proximal direction, that is, in the direction of arrow 240. Piston 238 has an integrally formed sterility skirt 242 having a folded back portion 244 which is secured against the surface portion 200 of assembly 186 by a sealing ring 246.

Manifold cover 216 has a threaded boss 248 to which an internally threaded needle hub 250 can be mounted. A hollow needle canula 252 is secured to needle hub 250 by a suitable epoxy 254. Needle hub 250, hollow needle 252, and epoxy 254 constitute a needle assembly 262 such as one sold by the Becton Dickenson Company of Rutherford, New Jersey, which is packaged in an outer sheath 264. Needle assembly 262 is sealed within outer sheath 264 by a removable film strip, not shown, secured to an edge 266 of sheath 264.

Needle 252 has a sharpened inner end 256 which pierces that portion 258 of manifold check valve 208 covering the end of blind bore 206 when needle assembly 262 is mounted to 248. This occurs after the desired mixture of pharmaceuticals 226, 228 has been accumulated in chamber 202. Needle 252 is generally covered by a sheath 260 for safety and sanitary purposes. Needle assembly 262 and sheath 264 are typically disposed of after each use. Outer sheath 264 not only protects needle assembly 262 against damage and contamination, but sheath 264 is also used while metering liquid pharmaceuticals 226, 228 from cartridges 182, 184 and into accumulator chamber 202 as will be discussed in detail below.

Pistons 224, 225 are driven by stem assemblies 268, 270 which are housed within proximal ends 174, 176. Stem assemblies 268, 270 include externally threaded stems 272, 274 sized to fit within hollow stem drivers 276, 278. Stem drivers 276, 278 have internal threads 280, 282 which engage the external threads 284, 286 formed along substantially the entire lengths of stems 272, 274. The distal ends 288, 290 of stem drivers 276, 278 have four slits 292 formed therein. Slits 292 permit distal ends 288, 290 to separate to permit stems 272, 274 to move axially within stem drivers 276, 278 by permitting the threads to override one another. Stem assemblies 268, 270 also include locking collars 294, 296 sized to fit over the outside of stem drivers 276, 278. As shown in FIGS. 13B and 13C, locking collars are axially positioned using a button 298 mounted within a cutout 300 formed in body 162. A pair of pins 302 extend from button 298, pass through slots 304, 306 to engage locking collars 294, 296. By manipulation of axially movable button 298, locking collars 294, 296 can be moved from the locked position of FIG. 12 overlying distal ends 288, 290 to a position to the right relative to FIG. 12, thus permitting distal ends 288, 290 to expand when stems 272, 274 are pulled from or pushed into stem drivers 276, 278.

Figure 28:
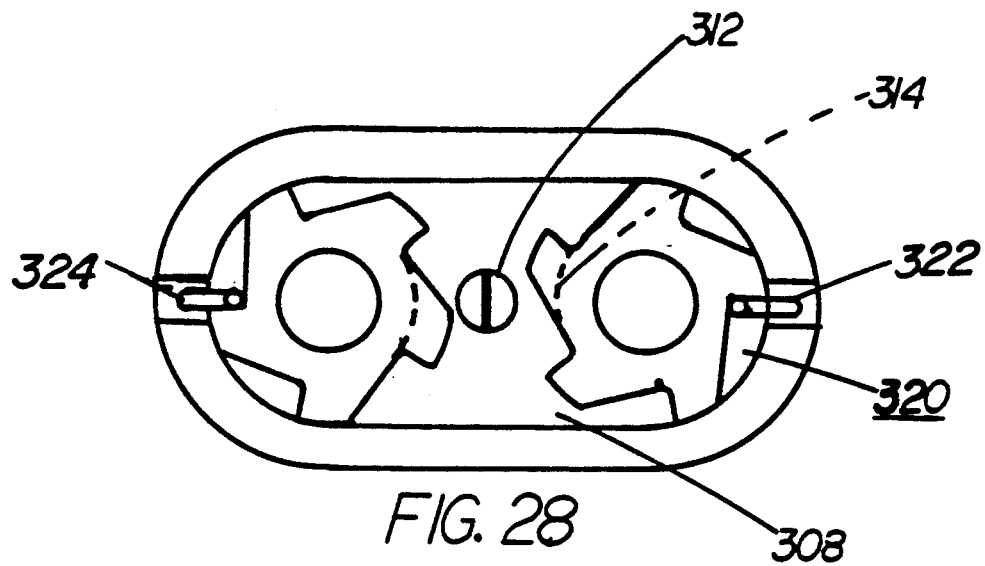
FIGS. 26–28 are simplified front, side and end views illustrating the detent mechanisms used with the stem drivers of FIG. 16.
Figure 26:
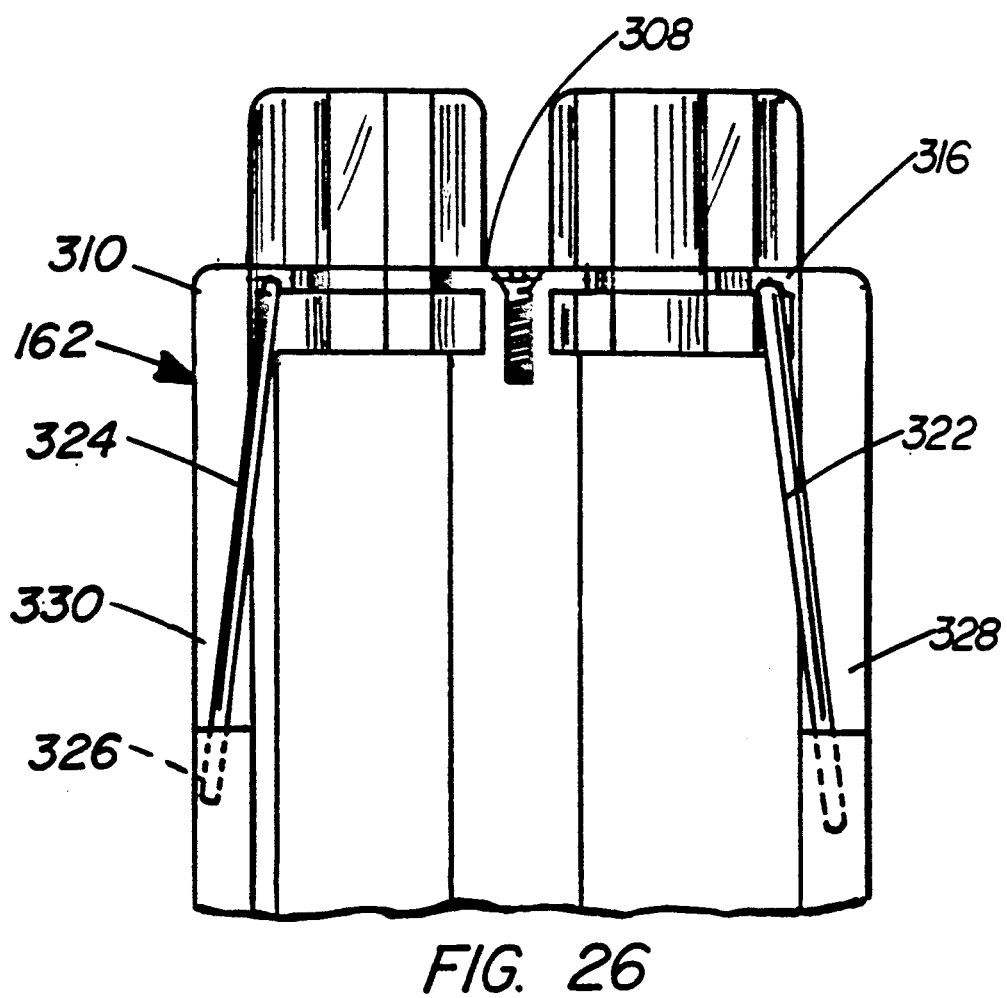
Figure 27:
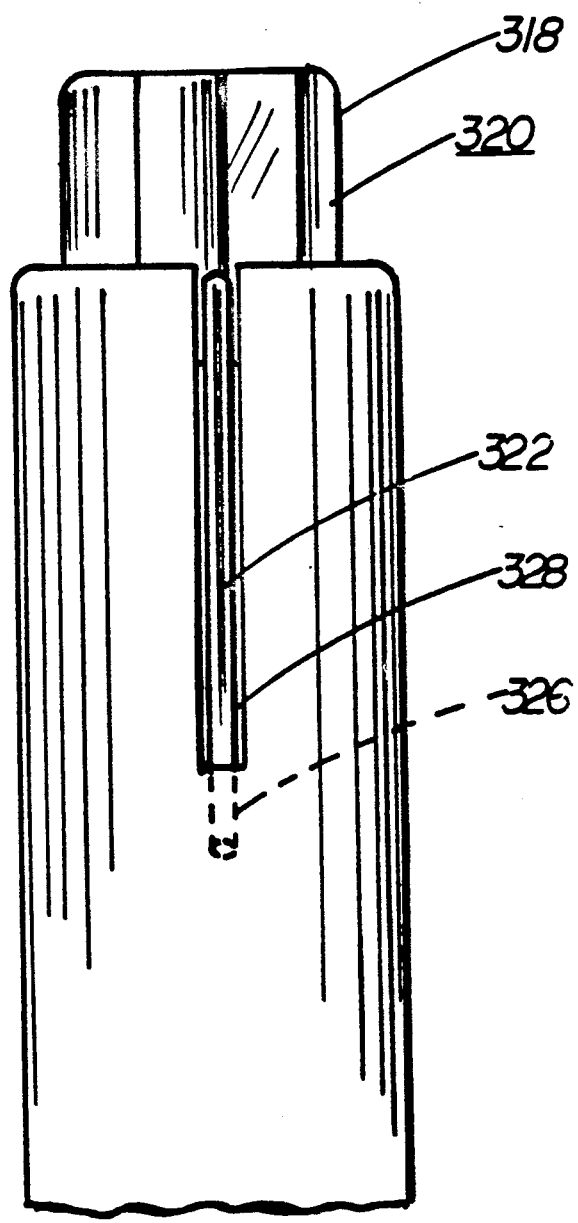

Stem drivers 276, 278 are free to rotate within proximal ends 174, 176 but are retained therein by a yoke 308, see FIGS. 26-28, which is secured to the proximal end 310 of body 162 by a screw 312. Yoke 308 has a pair of arcuate cutouts 314 which fit within annular slots 316 formed in the proximal ends 318 of stem drivers 276, 278. Proximal ends 318 include a ratcheted outer surface 320. Spring wires 322, 324 are mounted within holes 326 at the end of slots 328, 330. Holes 328, 330 are formed at an angle so that spring wires 322, 324 press against ratcheted outer surfaces 320 of stem drivers 276, 278.

As the user rotates stem drivers 276, 278, the stem drivers remain axially in place but cause stems 274, 276 to press against pistons 224, 225 respectively. Doing so causes the pharmaceuticals 226, 228 to enter accumulator chamber 202 and drive accumulator piston 238 to the right in FIG. 12. Needle assembly 262 is then mounted to threaded boss 248 so that sharpened inner end 256 pierces portion 258 of manifold check valve 208. The movement of piston 238 to the right in FIG. 12, that is in the proximal direction, causes an accumulator stem 332 to move to the right in FIG. 12. This causes a thumb driver assembly 334 mounted to the proximal end 336 to also move to the right in FIG. 12. To make the injection, pivotal thumb support 336 is pivoted in the direction of arrow 338 of FIG. 13. Sheath 260 is then removed and the injection is given by pressing on thumb support 336.

As suggested in FIG. 12, outer sheath 264 can be used to provide the user with an additional mechanical advantage in the rotation of stem drivers 276, 278. Proximal ends 318 have tapered openings 340 sized to frictionally engage the tapered outer surface of outer surface 342 of outer sheath 264.

Referring now to FIGS. 13A, 23, 24 and 25, syringe 160 is seen to include an optical dose indicator 346 pivotally mounted to body 162. Indicator 346 includes a frame 348 having a pair of cutouts 350. Within each cutout 350 is a support surface 352 and a guide slot 354 defined within a guide slot extension 356. A continuous loop indicator ribbon 358 having a line of demarcation 360 is positioned over and around each support surface 352. A follower 362 having a pair of slots 364 on its upper end is mounted within slot 354 for movement along the slot. Follower 362 includes a ribbon gripper 366 which securely grips ribbon 358 along its lower reach.

Figure 13:
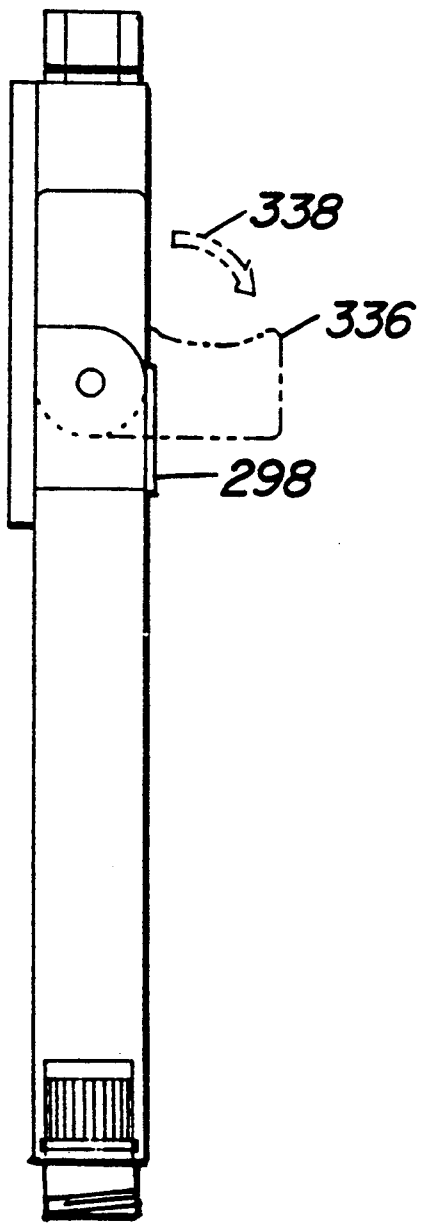
Figure 13A:
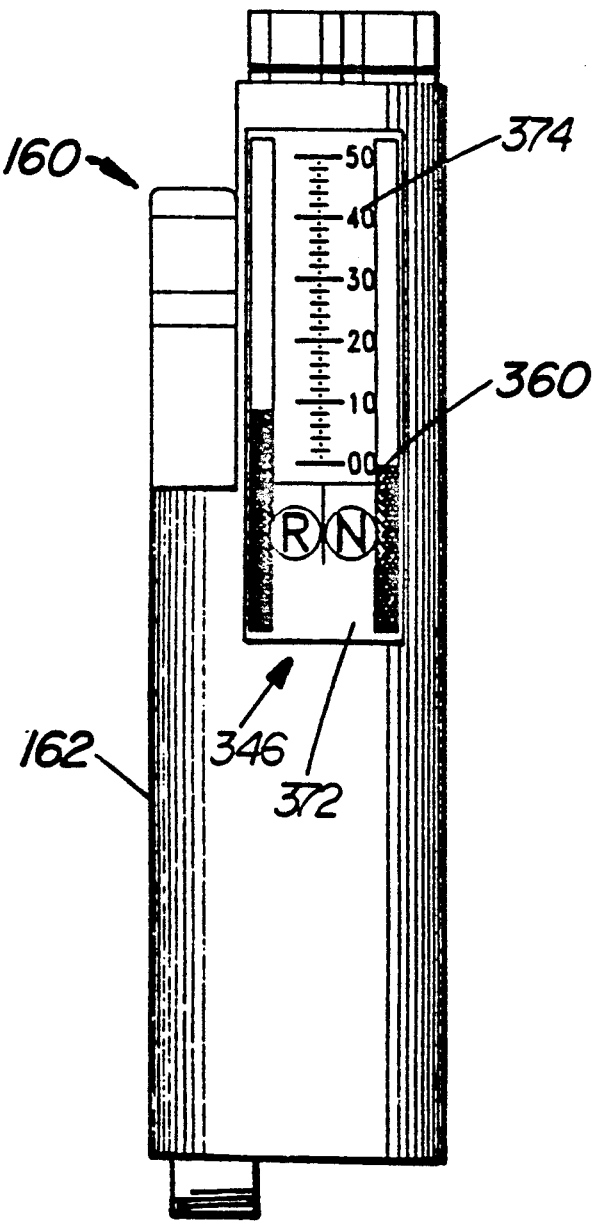
Figure 16:
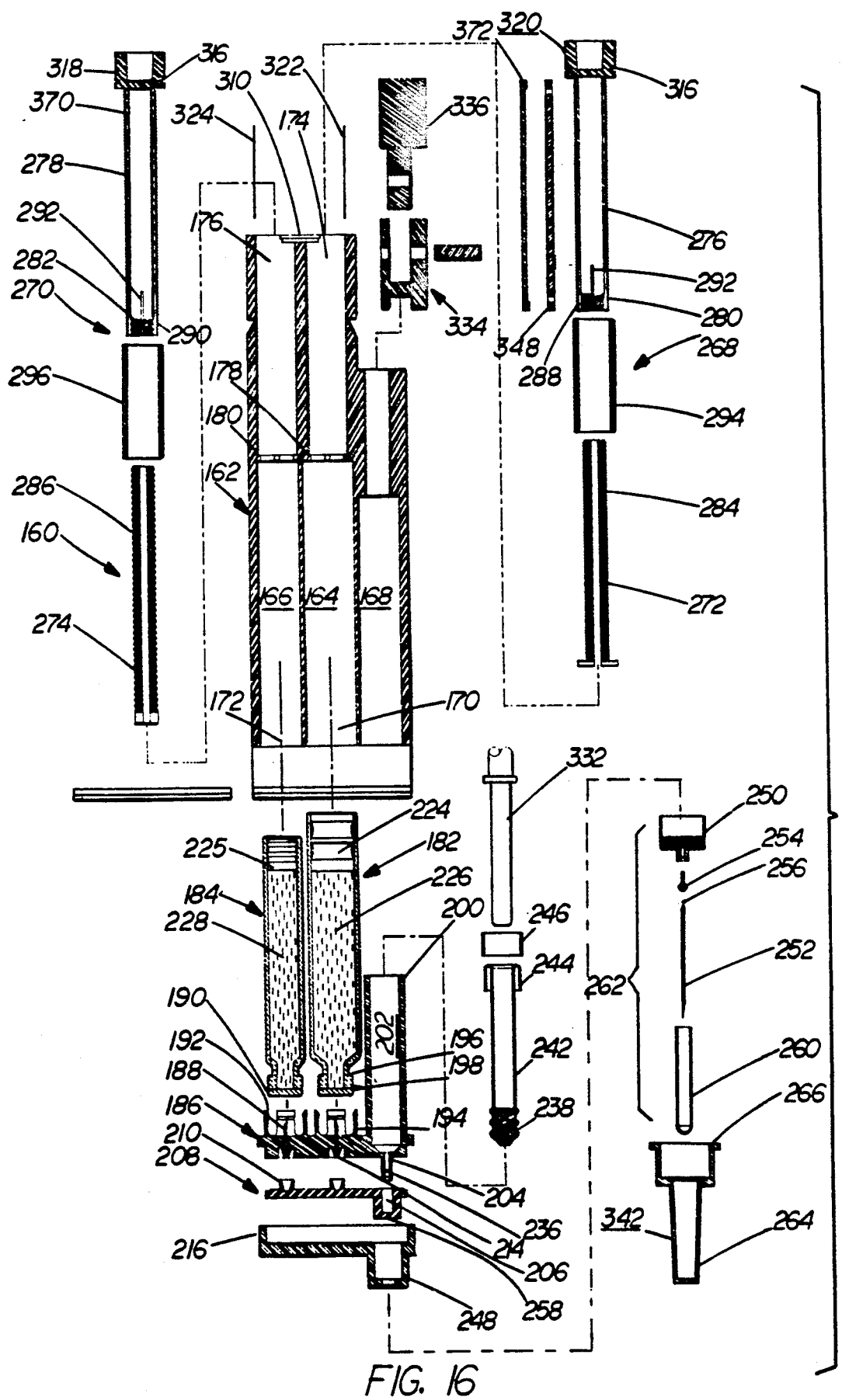
FIG. 16 is an exploded cross-sectional view of the syringe of FIG. 12.
Figure 17:
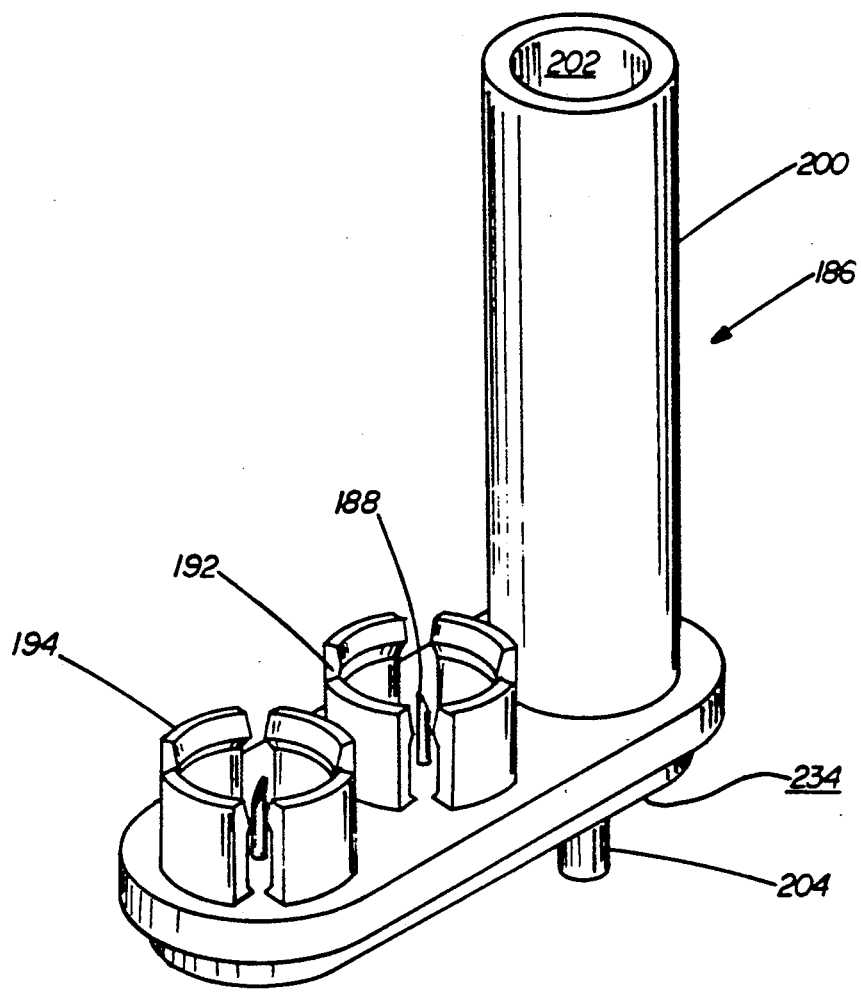
FIG. 17 is an isometric view of the manifold base and accumulator chamber assembly of FIG. 16.

Follower 362 has teeth 368 sized to engage teeth 370 formed on the outer surface of stem drivers 276, 278. FIG. 16 illustrates frame 348 with a clear cover 372 positioned above the frame. Cover 372, as shown in FIG. 13A, has numerical indicia 374 on cover 372. This permits the user to clearly determine the size of the dose, typically in units of medicine, by the location of line of demarcation 360 relative to indicia 374. It is preferred that follower 362, and thus line of demarcation 360, move at a greater linear speed than the corresponding piston 224, 225. In preferred embodiment, this is a 2 to 1 ratio so that if external threads 284 are spaced at 20 threads per inch, teeth 370 are spaced at 10 threads per inch for a 2 times amplification. Since the distances moved are generally relatively small, this can be a great help to the user, especially those who are visually impaired.

Other modification and variation can be made to the disclosed embodiments without departing from the subject of the invention as defined in the following claims. For example, syringe 2 could be modified so that an empty, generally conventional cartridge is used as accumulator chamber 10. The needle assembly could be pivotally mounted to the syringe body. The needle assembly could also be permanently mounted in place. Instead of using check valves 58, 59, pistons 42, 44 could be made to be movable in one direction only, towards far end 38, to prevent the reverse flow of liquid back into the cartridges. The syringe could be made for use with more than two cartridges. The invention may also include an additional cartridge or chamber containing sterile saline solution useful for flushing out the hollow needle and fluid pathway downstream of the spikes after an injection.

What is claimed is:

1. A syringe, for use with liquid-filled pharmaceutical cartridges of the type having a barrel, the barrel having an open end and an accessible end, a piston within the interior of the barrel and a liquid within the barrel between the piston and the accessible end, comprising:
   a body configured to house first and second of the cartridges therein;
   a replaceable fluid path assembly mountable to the body, comprising;
      an elongate accumulator chamber;
      a movable accumulator piston housed within the accumulator chamber;
      first means, engageable with the accessible ends of the first and second cartridges, for fluidly coupling the interiors of the barrels of the first and second cartridges to the accumulator chamber; and
   means for preventing fluid flow into the interiors of the barrels of the first and second cartridges;
   a hollow needle;
   means for selectively fluidly coupling the hollow needle with the accumulator chamber; and
   stem means engageable with the cartridge pistons and the accumulator piston by which selected amounts of liquid from the first and second cartridges are forcible by the stem into the accumulator chamber to mix within the accumulator chamber, the mixed liquid in the accumulator chamber being forcible by the stem through the selectively fluidly coupling means and through the hollow needle.

2. The syringe of claim 1 wherein the first fluidly coupling means include hollow spikes for piercing the accessible ends of the first and second cartridges.

3. The syringe of claim 1 wherein the fluid flow preventing means includes a one-way check valve for each of said first and second cartridges.

4. The syringe of claim 1 wherein the selectively fluidly coupling means includes a needle hub mountable to the replaceable fluid path assembly.

5. The syringe of claim 4 wherein the coupling means includes a removable needle sheath mounted to the needle hub.

6. The syringe of claim 1 wherein the accumulator chamber includes a distal end and a proximal end, the stem means including an accumulator stem extending from the proximal end.

7. The syringe of claim 1, wherein the body has portions constructed to enable the user to view the cartridges and the accumulator chamber.

8. The syringe of claim 1 further comprising calibration markings on said body to allow the user to gauge the amounts of liquids forced from the cartridges to the accumulator chamber.

* * * * *